(12) United States Patent
Dakshanamurthy et al.

(10) Patent No.: US 11,179,395 B2
(45) Date of Patent: Nov. 23, 2021

(54) TREATING MELANOMA WITH MEBENDAZOLE AND A MITOGEN-ACTIVATED KINASE INHIBITOR

(71) Applicant: GEORGETOWN UNIVERSITY, Washington, DC (US)

(72) Inventors: Sivanesan Dakshanamurthy, Herndon, VA (US); Stephen W. Byers, Takoma Park, MD (US); Dean Rosenthal, Gaithersburg, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 15/923,244

(22) Filed: Mar. 16, 2018

(65) Prior Publication Data

US 2018/0263987 A1    Sep. 20, 2018

Related U.S. Application Data

(60) Provisional application No. 62/472,374, filed on Mar. 16, 2017.

(51) Int. Cl.
| | | |
|---|---|---|
| *A61K 31/519* | (2006.01) | |
| *A61P 35/00* | (2006.01) | |
| *A61K 31/4184* | (2006.01) | |
| *C12Q 1/6886* | (2018.01) | |

(52) U.S. Cl.
CPC ........ *A61K 31/519* (2013.01); *A61K 31/4184* (2013.01); *A61P 35/00* (2018.01); *C12Q 1/6886* (2013.01); *C12Q 2600/106* (2013.01); *C12Q 2600/156* (2013.01)

(58) Field of Classification Search
CPC .... A61K 31/519; A61K 31/4184; A61P 35/00
See application file for complete search history.

(56) References Cited

U.S. PATENT DOCUMENTS

2012/0064008 A1* 3/2012 Zetter ................. A61K 9/0019
424/9.2

OTHER PUBLICATIONS

Flaherty et al. Combined BRAF and MEK inhibition in melanoma and BRAF V600 mutations. N. Engl. J. Med. 2012; 367: 1694-703.*
Falchook et al. Activity of the oral MEK inhibitor trametinib in patients with advanced melanoma: a phase 1 dose-escalation trial. Lancet Oncol., 2012; 13: 782-89.*
Doudican et al. XIAP downregulation accompanies mebendazole growth inhibition in melanoma xenografts. Anti-Cancer Drugs, 2013, 24: 181-188.*
Nygren et al. Repositioning of the anthelmintic durg mebendazole for the treatment of colon cancer. (J. Cancer Res. Clin. Oncol, 2013, 139: 2133-2140).*

Chou and Talalay. Quantitative Analysis of Dose-Effect Relationships: The combined effects of multiple drugs or enzyme inhibitors. Advances in Enzyme Regulation, 22, 27-55, 1984.*
Argyriou et al., "Chemotherapy-Induced Peripheral Neuropathy in Adults: A Comprehensive Update of the Literature", Cancer Management and Research, vol. 6, No. 1, Mar. 19, 2014, pp. 135-147.
Bai et al., "Brain Penetration and Efficacy of Different Mebendazole Polymorphs in a Mouse Brain Tumor Model", Clinical Cancer Research, vol. 21, No. 15, Aug. 1, 2015, pp. 3462-3470.
Ball et al., "Ras Mutations in Human Melanoma: A Marker of Malignant Progression", Journal of Investigative Dermatology, vol. 102, No. 3, Mar. 1994, pp. 285-290.
Banerjee et al., "Mebendazole (R-17,635): A New Anthelmintic in the Development of Hookworms", Transactions of The Royal Society of Tropical Medicine and Hygiene, vol. 65, No. 5, Jan. 1, 1971, pp. 685-686.
Bekhti et al., "Cimetidine Increases Serum Mebendazole Concentrations. Implications for Treatment of Hepatic Hydatid Cysts", Br. J. Clinical Pharmacol, vol. 24, No. 3, Sep. 1987, pp. 390-392.
Berenbaum et al., "Synergy, Additivism and Antagonism in Immunosuppression. A Critical Review", Clinical & Experimental Immunology, vol. 28, No. 1, Apr. 1977, pp. 1-18.
Bollag et al., "Vemurafenib: The First Drug Approved for BRAF-Mutant Cancer", Nature Reviews Drug Discovery, Case Histories, vol. 11, Nov. 2012, pp. 873-886.
Boucher et al., "MEK/ERK Signaling Pathway Regulates the Expression of Bcl-2, Bcl-X(L), and Mcl-1 and Promotes Survival of Human Pancreatic Cancer Cells", Journal of Cellular Biochemistry, vol. 79, No. 3, Sep. 7, 2000 , pp. 355-369.
Braithwaite et al., "Clinical Pharmacokinetics of High Dose Mebendazole in Patients Treated for Cystic Hydatid Disease", European Journal of Clinical Pharmacology, vol. 22, No. 2, 1982, pp. 161-169.
Curtin et al., "Distinct Sets of Genetic Alterations in Melanoma", New England Journal of Medicine, vol. 353, No. 20, Nov. 17, 2005, pp. 2135-2147.
Dakshanamurthy et al., "Predicting New Indications for Approved Drugs Using a Proteochemometric Method", J. Med. Chem., vol. 55, 2012, pp. 6832-6848.
Dobrosotskaya et al., "Mebendazole Monotherapy and Long-Term Disease Control in Metastatic Adrenocortical Carcinoma", Endocrine Practice, vol. 17, No. 3, May-Jun. 2011, pp. e59-e62.
Doudican et al., "Mebendazole Induces Apoptosis via Bcl-2 Inactivation in Chemoresistant Melanoma Cells", Molecular Cancer Research, vol. 6, No. 8, Aug. 2008, pp. 1308-1315.
Einspahr et al., "Functional Protein Pathway Activation Mapping of the Progression of Normal Skin to Squamous Cell Carcinoma", Cancer Prevention Research (Phila), vol. 5, No. 3, Mar. 2012, pp. 403-413.
Freireich et al., "Quantitative Comparison of Toxicity of Anticancer Agents in Mouse, Rat, Hamster, Dog, Monkey, and Man", Cancer Chemotherapy Reports, vol. 50, No. 4, May 1, 1966, pp. 219-244.
Friedman et al., "Interaction of Anthelmintic Benzimidazoles with Ascaris Suum Embryonic Tubulin", Biochimica et Biophysica Acta, vol. 630, No. 2, Jun. 19, 1980, pp. 271-278.
Hather et al., "Growth Rate Analysis and Efficient Experimental Design for Tumor Xenograft Studies", Cancer Informatics, vol. 13, Supplemental 4, Aug. 12, 2014, pp. 65-72.

(Continued)

*Primary Examiner* — Anna Pagonakis
(74) *Attorney, Agent, or Firm* — Kilpatrick Townsend & Stockton LLP

(57) ABSTRACT

Provided herein are methods for treating melanoma in a subject.

4 Claims, 18 Drawing Sheets

(56) References Cited

OTHER PUBLICATIONS

Hatzivassiliou et al., "RAF Inhibitors Prime Wild-Type RAF to Activate the MAPK Pathway and Enhance Growth", Nature, vol. 464, Mar. 18, 2010, pp. 431-435.
Hayakawa et al., "Inhibition of BAD Phosphorylation Either at Serine 112 via Extracellular Signal-Regulated Protein Kinase Cascade or at Serine 136 via Akt Cascade Sensitizes Human Ovarian Cancer Cells to Cisplatin", Cancer Research, vol. 60, Nov. 1, 2000, pp. 5988-5994.
Issa et al., "RepurposeVS: A Drug Repurposing-Focused Computational Method for Accurate Drug-Target Signature Predictions", Combinatorial Chemistry & High Throughput Screening, vol. 18, No. 8, 2015, pp. 784-794.
Jang et al., "BH3-Mimetic Gossypol-Induced Autophagic Cell Death in Mutant BRAF Melanoma Cells with High Expression of p21Cip1", Life Sciences, vol. 102, No. 1, Apr. 25, 2014, pp. 41-48.
Kim et al., "Raf/MEK/ERK can Regulate Cellular Levels of LC3B and SQSTM1/p62 at Expression Levels", Experimental Cell Research, vol. 327, No. 2, Oct. 1, 2014, pp. 340-352.
Kollmannsberger et al., "Sunitinib in Metastatic Renal Cell Carcinoma: Recommendations for Management of Noncardiovascular Toxicities", Oncologist, vol. 16, No. 5, May 2011, pp. 543-553.
Laclette et al., "Inhibition of Tubulin Polymerization by Mebendazole", Biochemical and Biophysical Research Communications, vol. 92, No. 2, Jan. 29, 1980, pp. 417-423.
Lovly et al., "Molecular Pathways: Resistance to Kinase Inhibitors and Implications for Therapeutic Strategies", Clinical Cancer Research, vol. 20, No. 9, May 1, 2014, pp. 2249-2256.
Messaritakis et al., "High Mebendazole Doses in Pulmonary and Hepatic Hydatid Disease", Archives of Disease in Childhood, vol. 66, No. 4, Apr. 1991, pp. 532-533.
Mosteller et al., "Simplified Calculation of Body-Surface Area", The New England Journal of Medicine, vol. 317, No. 17, Oct. 22, 1987, p. 1098.
Mukhopadhyay et al., "Mebendazole Elicits a Potent Antitumor Effect on Human Cancer Cell Lines Both in Vitro and in Vivo", Clinical Cancer Research, vol. 8, No. 9, Sep. 2002, pp. 2963-2969.
Niculescu-Duvaz et al., "Novel Tricyclic Pyrazole BRAF Inhibitors with Imidazole or Furan Central Scaffolds", Bioorganic & Medicinal Chemistry, vol. 18, No. 18, Sep. 15, 2010, pp. 6934-6952.
Nygren et al., "Drug Repositioning from Bench to Bedside: Tumour Remission by the Antihelmintic Drug Mebendazole in Refractory Metastatic Colon Cancer", Acta Oncologica, vol. 53, No. 3, Mar. 2014, pp. 427-428.
Panjawani, "Nilotinib/Trametinib Show Early Promise in BRAF/NRAS Wild-Type Melanoma", OncLive, Available online at: https://www.onclive.com/conference-coverage/smr-2016/nilotinibtrametinib-show-early-promise-in-brafnras-wildtype-melanoma, Nov. 9, 2016, 3 pages.
Pantziarka et al., "Repurposing Drugs in Oncology (ReDO)—mebendazole as an Anti-Cancer Agent", ecancermedicalscience, vol. 8, No. 443, Jul. 10, 2014, pp. 1-16.
Paul et al., "How to Improve R&D Productivity: The Pharmaceutical Industry's Grand Challenge", Nature Reviews Drug Discovery, vol. 9, No. 3, Mar. 2010, pp. 203-214.
Platz et al., "Human Cutaneous Melanoma; A Review of NRAS and BRAF Mutation Frequencies in Relation to Histogenetic Subclass and Body Site", Molecular Oncology, vol. 1, No. 4, Apr. 2008, pp. 395-405.
Sasaki et al., "The Anthelmintic Drug Mebendazole Induces Mitotic Arrest and Apoptosis by Depolymerizing Tubulin in Non-Small Cell Lung Cancer Cells", Molecular Cancer Therapeutics, vol. 1, No. 13, Nov. 2002, pp. 1201-1209.
Simbulan-Rosenthal et al., "HPV-16 E6/7 Immortalization Sensitizes Human Keratinocytes to Ultraviolet B by Altering the Pathway from Caspase-8 to Caspase-9-Dependent Apoptosis", Journal of Biological Chemistry, vol. 277, No. 27, Jul. 5, 2002, p. 24709-24716.
Simbulan-Rosenthal et al., "The Repurposed Anthelmintic Mebendazole in Combination with Trametinib Suppresses Refractory NRASQ61K Melanoma", Oncotarget, Priority Research Paper, vol. 8, No. 8, Feb. 2, 2017, pp. 12576-12595.
Sun et al., "Sorafenib Induces Endometrial Carcinoma Apoptosis by Inhibiting Elk-1-Dependent Mcl-1 Transcription and Inducing Akt/GSK3beta-Dependent Protein Degradation", J Cell Biochem, vol. 114, No. 8, Aug. 2013, pp. 1819-1831.
Tseng et al., "Use of DNA Microarray and Small Animal Positron Emission Tomography in Preclinical Drug Evaluation of RAF265, A Novel B-Raf/VEGFR-2 Inhibitor", Neoplasia, vol. 13, No. 3, Mar. 2011, pp. 266-275.
Van 't Veer et al., "N-Ras Mutations in Human Cutaneous Melanoma from Sun-Exposed Body Sites", Molecular and Cellular Biology, vol. 9, No. 7, Jul. 1989, pp. 3114-3116.
Wan et al., "Mechanism of Activation of the RAF-ERK Signaling Pathway by Oncogenic Mutations of B-RAF", Cell, vol. 116, No. 6, Mar. 19, 2004, pp. 855-867.

\* cited by examiner

| Kinase Target | Percent Control at 10 μM | Binding Affinity $K_d$ (nM) |
|---|---|---|
| BRAF | 7.8 | 230 |
| BRAF (V600E) | 3.2 | 210 |
| MEK1 | 16 | NA |
| MEK2 | 12 | NA |
| C-RAF | 23 | NA |
| VEGFR2 | 20 | 3,200 |

FIGURE 1C

TREATING MELANOMA WITH MEBENDAZOLE AND A MITOGEN-ACTIVATED KINASE INHIBITOR

CROSS-REFERENCE TO PRIORITY APPLICATIONS

This application claims priority to U.S. Provisional Application No. 62/472,374, filed Mar. 16, 2017, the entirety of which is incorporated by reference herein.

BACKGROUND

It is estimated that, in 2017, about 87,110 new skin melanomas will be diagnosed and 9,940 people are expected to die of melanoma. Despite recent advances in treatment, the majority of patients with metastatic melanoma are likely to die of their disease.

SUMMARY

Provided herein are methods for treating melanoma in a subject. The methods comprise administering, to a subject with melanoma, a wildtype BRAF inhibitor and a mitogen-activated protein kinase (MEK) inhibitor.

BRIEF DESCRIPTION OF THE FIGURES

FIG. 1C is a table showing MBZ inhibition of kinase activity and binding affinities for different targets.

DETAILED DESCRIPTION

Figure 1A:
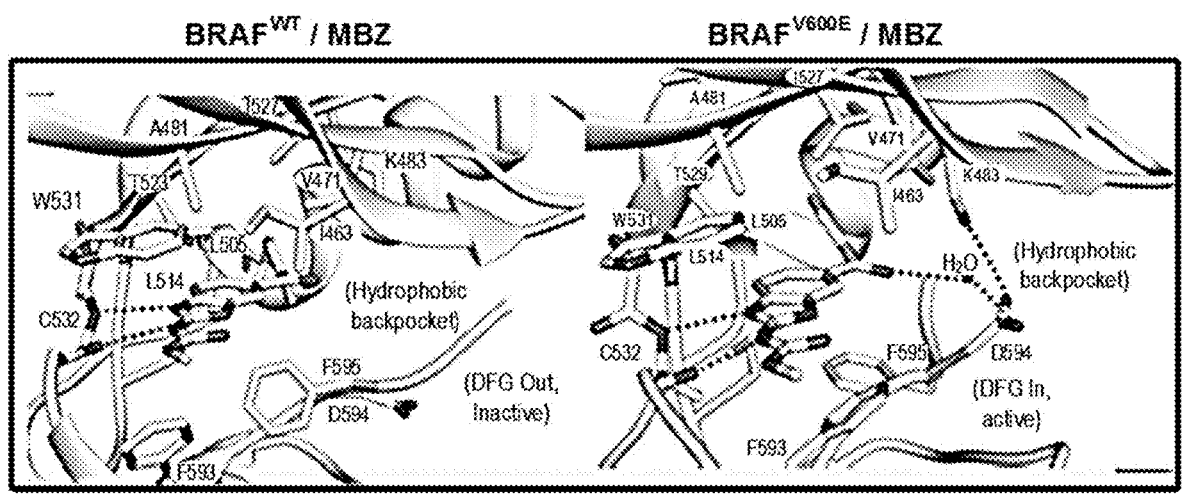
FIG. 1A shows the structure of mebendazole (MBZ) with wildtype BRAF (BRAFWT) (left) or BRAFV600E (right), showing residues critical for binding; hydrogen bonds are shown as dotted lines.

Mebendazole (MBZ; methyl N-[6-(benzoyl)-1H-benzimidazol-2-yl] carbamate), an inexpensive chewable antihelmintic drug, has been widely used since the early 1970s, for the treatment of roundworm infection, and is non-toxic even when administered in high doses. MBZ acts at the colchicine-binding site of roundworm tubulin, and disrupts its polymerization. MBZ does not cause side effects characteristic of other anti-microtubule drugs, including taxanes and the vinca alkaloids.

Current cancer therapies have focused on targeting driver mutations, including oncogenic BRAF and NRAS, which are frequent in melanomas. BRAFV600E and BRAFV600K are found in 46% and 9% of melanomas, respectively. Additionally, 10% of melanomas previously classified as BRAFWT tumors actually harbor non-V600E/K mutations in BRAF. In fact, more than 30 mutations of the BRAF gene associated with human cancers have been identified, many of which may be sensitive to trametinib since these show deregulated stimulation of MEK1/2. Acquired resistance to the targeted therapeutics dabrafenib (GSK 2118436a; a BRAFV600E/K inhibitor) and/or trametinib (GSK1120212; a MEK1/2 inhibitor) is associated with development of additional mutations, including those activating NRAS. Patients with BRAFWT melanomas, including those harboring NRASmut/BRAFWT signatures (~21% of patients) have limited treatment options and are refractory to current targeted therapies.

Provided herein is a method for treating melanoma comprising administering to a subject with melanoma a wildtype BRAF inhibitor and a mitogen-activated protein kinase (MEK) inhibitor. BRAF or B-RAF is a member of the Raf kinase family of growth signal transduction protein kinases that is encoded by the BRAF gene This protein is involved in regulating the MAP kinase/ERKs signaling pathway, which affects cell division, differentiation and secretion. In any of the methods provided herein, the subject can be diagnosed with melanoma prior to treatment. The subject can also be diagnosed as a subject having a wildtype BRAF (BRAFWT) melanoma tumor prior to treatment.

As used throughout, a melanoma or melanoma tumor is a type of skin cancer that develops in melanocytes. Exposure to ultraviolet radiation from sunlight or tanning lamps increases the risk of developing melanoma.

In any of the methods provided herein, the wildtype BRAF inhibitor or wildtype BRAF antagonist, is an inhibitor that inhibits a wildtype BRAF protein, i.e., a non-mutated BRAF protein or a mutated BRAF protein for which a specific mutation was not detected during genetic testing. For example, a melanoma tumor may be characterized as a wildtype BRAF tumor if no mutation in a particular genetic screen is detected in a tumor sample from the subject. In some methods, the wildtype BRAF inhibitor inhibits a wildtype BRAF protein that is activated when a melanoma tumor acquires resistance to therapy, for example, resistance to anti-mutant BRAF therapy. The wildtype BRAF inhibitor can selectively or preferentially inhibit wildtype BRAF or the wildtype BRAF inhibitor can inhibit wildtype BRAF protein and mutated BRAF protein. For example, and not to be limiting, the wildtype BRAF inhibitor can be mebendazole (MBZ) or a pharmaceutically acceptable salt thereof. As shown in the Examples, MBZ is an inhibitor of wildtype BRAF and mutated BRAF.

In any of the methods provided herein, the MEK inhibitor can be any MEK inhibitor that inhibits the mitogen-activated protein kinase enzymes MEK1 and/or MEK2. The MEK inhibitor can modulate the MAPK/ERK pathway in melanoma. Examples of MEK inhibitors include, but are not limited to, Tramatenib (GSK1120212), Cobimetinib (SL518), Binimetinium (Mek162), Selumetinib, PD-325901, CI-1040, PD035901, TAK-733 and derivatives thereof. Pharmaceutically acceptable salts of the MEK inhibitors and derivatives thereof described herein can also be used in any of the methods provided herein.

As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetic acid, undecanoate, valerate salts, and the like.

Optionally, in any of the methods provided herein, the wildtype BRAF inhibitor synergizes with the MEK inhibitor to inhibit melanoma growth, decrease MEK phosphorylation and/or ERK phosphorylation.

Any of the methods provided herein can further comprise determining the mutational status of the subject. The mutational status can be determined prior to treatment with a wildtype BRAF inhibitor and an MEK inhibitor, after treatment with anti-mutant BRAF therapy, before acquiring resistance to any treatment for malenoma or after acquiring resistance to any treatment for melanoma. For example, the mutational status of the BRAF gene, the NRAS gene, and/or the CKIT gene can be determined. More than 30 mutations of the BRAF gene associated with human cancers have been identified. These mutations include, but are not limited to, one or more mutations that result in a V600D, V600G, V600R, V600E, V600K, R462I, I463S, G464E, G464R, G464V, G466A, G469A, G469E, N581S, E586K, F595L, L597Q, L597R, L597S, L597V, A598V, T599E, T599I, S602D and/or a A728V mutation in a wildtype BRAF. These mutations are substitutions where an amino acid is substituted with another amino acid. For example, A V600E BRAF mutant is a BRAF protein where a valine (V) is substituted with glutamate (E) at amino acid position 600 of wildtype BRAF. An example of a wildtype amino acid sequence for BRAF can be found under Genbank Accession No. NP_004324, hereby incorporated by this reference. The locations of the amino acids of BRAF set forth herein are based on the wildtype sequence set forth under Genbank Accession No. NP_004324. However, it is understood that the corresponding positions in other BRAF proteins can be mutated.

Mutations in the NRAS gene include, but are not limited to, one or more mutations that result in a Q61R, Q61L, Q61K, Q61P, G12A, G12C, G12D, G12R, G12S, G12V, G13A, G13C, G13D, G13R, G13S and/or a G13V mutation in a NRAS protein, for example, a wildtype NRAS protein. An example of a wildtype amino acid sequence for NRAS can be found under Genbank Accession No. NP_002515.1, hereby incorporated by this reference. The locations of the amino acids of NRAS set forth herein are based on the wildtype sequence set forth under Genbank Accession No. NP_002515.1. However, it is understood that the corresponding positions in other NRAS proteins can be mutated.

Mutations in the CKIT gene include, but are not limited to, one or more mutations that result in a N463S, G446E, G446R, Y553C, E554K, W557R, V559A, V559C, V559G, V560D, Y570H, L576P, K642E, L647F, G648D, I653T, V654A, L813P, K818Q, D820Y, N822K, N822Y, A829P, L831P, P838L, Y846C, S850G, L859P and/or a L862P mutation in a C-KIT protein, for example, a wildtype C-KIT protein. An example of a wildtype amino acid sequence for C-KIT can be found under Genbank Accession No. NP_000213.1, hereby incorporated by this reference. The locations of the amino acids of C-KIT set forth herein are based on the wildtype sequence set forth under Genbank Accession No. NP_000213.1. However, it is understood that the corresponding positions in other C-KIT proteins can be mutated.

In any of the methods provided herein, the subject can have one or more mutations in the BRAT gene, the NRAS gene and/or the CKIT gene. In any of the methods provided herein, the subject can have a wildtype BRAF gene, a wildtype NRAS gene and/or a wildtype CKIT gene. Determination of mutational status typically involves screening for one or more predetermined mutations in the BRAF gene, the NRAS gene and/or the CKIT gene. Therefore, one of skill in the art would appreciate that, although a BRAF, NRAS or CKIT gene may contain one or more mutations that are not included in the one or more predetermined mutations used to determine mutational status of the tumor, a melanoma tumor can be classified as a wildtype BRAF tumor, a wildtype NRAS tumor and/or a wildtype CKIT tumor if none of the predetermined mutations for a particular gene are identified in a genetic screen. In some methods provided herein, the subject has a wildtype BRAF (BRAFWT)/wildtype NRAS (NRASWT) tumor. In other methods provided herein, the subject has a wildtype BRAF (BRAFWT)/mutant NRAS (NRAS$^{MUT}$) tumor. In some methods, the tumor in the subject has a wildtype BRAF gene and a mutation in the NRAS gene that results in a mutation at amino acid at position 61 of the NRAS protein, for example, a Q61R, Q61L, Q61K or a Q61P mutation. In some methods, the tumor in the subject has a non-V600E mutant BRAF gene and a wildtype NRAS gene. In other methods, the tumor in the subject has a non-V600E mutant BRAF gene and a mutation in the NRAS gene that results in a mutation at amino acid at position 61 of the NRAS protein, for example, a Q61R, Q61L, Q61K or Q61P mutation.

Any of the methods provided herein can further comprise determining the resistance status of the subject. The resistance status of the subject can be determined prior to the subject acquiring resistance to a therapy for melanoma. For example, specific mutations that are indicative of resistance to one or more therapies for melanoma can be identified prior to treating the subject. In other examples, the resistance status of the subject is determined after treatment, for example after treatment with a mutant BRAF inhibitor and/or an MEK inhibitor. In some methods, the subject is resistant to MEK inhibitor monotherapy, for example, trametinib monotherapy. In other methods, the subject is resistant to treatment with mutant BRAF inhibitor monotherapy. In some methods, the subject is resistant to treatment with a combination of an MEK inhibitor and a mutant BRAF inhibitor, for example, treatment with trametinib and dabrafenib or treatment with trametinib and vemurafenib.

Any of the methods provided herein can optionally further include surgery or administering radiation therapy to the subject.

Throughout, treat, treating, and treatment refer to a method of reducing or delaying one or more effects or symptoms of melanoma. Treatment can also refer to a method of reducing the underlying pathology rather than just the symptoms. The effect of the administration to the subject can have the effect of, but is not limited to, reducing one or more symptoms (e.g., reduced pain, reduced size of the tumor, etc.) of the melanoma, an increase in survival time, a decrease in metastasis, a decrease in time before metastasis, a reduction in the severity of the melanoma (e.g., reduced rate of growth of a tumor or rate of metastasis), the complete ablation of the melanoma or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

In any of the methods provided herein, the wildtype BRAF inhibitor and the MEK inhibitor can be administered in an effective amount. The term effective amount, as used throughout, is defined as any amount necessary to produce a desired physiologic response, i.e., treatment of melanoma.

Exemplary dosage amounts for administration of a wildtype BRAF inhibitor or an MEK inhibitor in a mammal include doses from about 0.5 to about 200 mg/kg of body weight of active compound per day, which may be administered in a single dose or in the form of individual divided doses, such as from 1 to 4 times per day can be used. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 50 mg/kg of body weight of active compound per day, about 1 to about 40 mg/kg of body weight of active compound per day, about 1 to about 30 mg/kg of body weight of active compound per day, about 1 to about 20 mg/kg of body weight of active compound per day, about 50 mg/kg of body weight of active compound per day, about 45 mg/kg of body weight of active compound per day, about 40 mg/kg of body weight of active compound per day, about 35 mg/kg of body weight of active compound per day, about 30 mg/kg of body weight of active compound per day, about 25 mg/kg of body weight of active compound per day, about 20 mg/kg of body weight of active compound per day, about 15 mg/kg of body weight of active compound per day, about 12.5 mg/kg of body weight of active compound per day, about 10 mg/kg of body weight of active compound per day, or about 5 mg/kg of body weight of active compound per day. One of skill in the art would adjust the dosage as described below based on specific characteristics of the inhibitor and the subject receiving it.

In some methods, the dosage of mebendazole is lower than the antihelmintic dosage of mebendazole. For example, the dosage can be less than about 100 mg per day, for example less than about 90, 80, 70, 60, 50, 40, 30, 20, 10, 5, 4, 3, 2 or 1 mg per day. In other methods, the dosage is less than the dosage of mebendazole used to treat hyatid disease in children, or less than about 200 mg/kg per day, for example, less than about 200, 175, 150, 125, 100, 50, 25, 15, 10, 5, 4, 3, 2, 1 mg/kg or any other amount in between these dosages.

In some methods, the dosage of trametinib is from about 1 mg to about 10 mg per day. For example, the dosage can be about 1, 2, 3, 4, 5, 6, 7, 8, 9 or 10 mg per day. In some methods, the dosage of trametinib is lower than the chemotherapeutic dosage used for trametinib monotherapy or lower than the chemotherapeutic dosage used for trametinib when administered in combination with vemurafenib or dabrafenib. For example, less than about 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.03 or 0.01 mg per day. The dosage of trametinib can also be less than about 1.0, 0.9, 0.8, 0.7, 0.6, 0.5, 0.4, 0.3, 0.2, 0.1, 0.05, 0.03, 0.02, or 0.01 mg/kg.

Effective amounts and schedules for administering a wildtype BRAF inhibitor and an MEK inhibitor can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily.

Any of the wildtype BRAF inhibitors or MEK inhibitors described herein can be provided in a pharmaceutical composition. These include, for example, a pharmaceutical composition comprising a therapeutically effective amount of one or more wildtype BRAF inhibitors and a pharmaceutical carrier; a pharmaceutical composition comprising a therapeutically effective amount of one or more MEK inhibitors and a pharmaceutical carrier; and a pharmaceutical composition comprising a therapeutically effective amount of one or more CCK-R antagonists, one or more immune checkpoint inhibitors and a pharmaceutical carrier.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like.

Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intramuscularly, subcutaneously, intrarectally, intracavity or transdermally. Pharmaceutical compositions can also be delivered locally to the area in need of treatment, for example by topical application or local injection. Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The studies provided herein show that the combination of MBZ and trametinib suppresses proliferation of patient-derived melanoma cell lines harboring NRASmut/BRAFWT, as determined by gene sequencing, and significantly attenuates their growth in xenografts in immunocompromised mice. Reverse phase protein array (RPPA) based protein pathway activation mapping and immunoblot analyses revealed specific inhibition of the MAPK pathway and downstream regulation by MBZ or trametinib alone or in combination, within 10 minutes of drug treatment. At later time points, MBZ+trametinib induces markers of apoptosis, including proteolytic activation of caspase-3 and PARP cleavage, increased caspase activity as measured by fluorometric assays and increased levels of apoptotic sub-G1 cells. A reduction of cells in S phase was also observed in cells exposed to trametinib (by 24 h) or trametinib+MBZ (by 8 h), concurrent with an increase in G2 by 24 h and in G1 by 48 h. Thus, these results are consistent with the suppression of the MEK1/2 by trametinib and suppression of BRAFWT by MBZ, leading to the combinatorial rapid shutoff of ERK activity, as well as downstream targets of ERK. MBZ is therefore a viable nontoxic option that can be used to increase the effectiveness of trametinib in NRASmut/BRAFWT melanoma.

Example 1

Methods
Proteochemometric Methods

A novel, rapid computational proteochemometric method called "Train, Match, Fit, Streamline" (TMFS) was used to map new drug-target interaction space and predict new uses as described (Dakshanamurthy et al. *J. Med. Chem.* 55: 6832-48 (2012)). The TMFS method combines shape, topology and chemical signatures, including docking score and functional contact points of the ligand, to predict potential drug-target interactions with remarkable accuracy.

Establishment and Characterization of Primary Human Melanoma Cell Lines

Human melanoma cell lines were established from fresh metastatic tumor tissues of consenting patients. Tumors were analyzed for mutations in CKIT, BRAF, and NRAS by next generation sequencing. Single cell suspensions were prepared from freshly resected tumor tissue specimens by mechanical mincing; no enzymatic dissociation was used. Viable tumor cells were cultured in Iscove's Modified Dulbecco's Medium (IMDM) supplemented with 10% fetal bovine serum (FBS) and antibiotics. After overnight incubation at 37° C., in 5% $CO_2$, floating debris was discarded and fresh complete medium was added. Cultures were fed 2-3 times per week, replacing half of the spent medium. Melanoma cell lines were split when near confluence and sub-cultured at $4 \times 10^4$ viable cells per $cm^2$ surface area in flasks. Cultures were shown to be free of mycoplasma contamination using the MycoProbe™ mycoplasma detection kit (R&D Systems, Minneapolis, Minn., USA). To ensure that cultured cell lines were melanoma cells, each cell line was stained and analyzed by flow cytometry for melanoma-specific antigens MART-1, gp100, TRP75, or melanoma-associated chondroitin sulfate proteoglycan. All cell lines were early passages of less than 20.

Cell Culture

Patient-derived melanoma cell lines (BAK and BUL) with the same BRAFWT/NRASQ61K mutation signature, as well as a melanoma cell line (STU) harboring a BRAFV600K/NRASWT mutation were cultured in IMDM with 10% FBS and 1% penicillin/streptomycin in a 5% $CO_2$ incubator at 37° C. Cell growth was monitored daily and expanded to obtain sufficient cell numbers for subsequent experiments. Mutation signatures of cell lines were confirmed by PCR and sequencing.

Drug Toxicity Assays

MBZ, dabrafenib, and trametinib were purchased from Sigma-Aldrich (St. Louis, Mo.) and ActiveBiochem (Maplewood, N.J.), respectively. $5 \times 10^3$ viable cells per well were plated in 96-well dishes and allowed to recover for 12 h prior to drug treatment. Cells in triplicate wells were treated for up to 72 h (based on initial time course experiments showing maximal effects at that time point) with different concentrations of trametinib, dabrafenib, or MBZ alone, or a combination of MBZ and trametinib. Negative controls were exposed to vehicle DMSO in the same volumes. Cell viability was assessed by an XTT assay, according to a manufacturer's specifications (Biotium Inc (Fremont, Calif.)). Reduced XTT was measured by absorbance at 490 nm on a PerkinElmer Victor 3 (Duluth, Ga.) plate reader. Cells exposed to detergent served as a positive control.

Cell Cycle Analysis

Cells were collected, fixed in ethanol, stained with propidium iodide (PI) to determine DNA content, and analyzed by flow cytometry (FACStar Plus; BD BioSciences, San Jose, Calif.).

Pharmacokinetic Studies

In pharmacokinetic (PK) studies, MBZ was administered to athymic mice (described below) by oral gavage at a dose of 40 mg/kg in three different formulations (methylcellulose, oleic acid, or sesame oil/PBS) or methylcellulose in combination with cimetidine. MBZ and two metabolites, 2-Amino-5-benzoyl-1H bezimidizole (2ABB), and rac Dihydro MBZ (RDM), were quantified in mouse plasma as described in Bai et al., "Brain Penetration and Efficacy of Different Mebendazole Polymorphs in a Mouse Brain Tumor Model," *Clin. Cancer Res.* 21:3462-3470 (2015)).

Mouse Xenografting

All animal experiments were performed in accordance with the guidelines and approval of Georgetown University Animal Care and Use Committee. Athymic 6-week old male mice (Taconic (Hudson, N.Y.)) were acclimated to the Division of Comparative Medicine at Georgetown University a week prior to xenografting. $3 \times 10^6$ melanoma cells were resuspended in Matrigel and injected subcutaneously into the hind flanks of athymic mice using a 22-gauge needle. Tumor growth was measured with calipers, and drug treatment started when tumor volumes reached 100 $mm^3$, after which mice were monitored daily for drug efficacy, as well for adverse effects, including weight and behavior. Drugs were administered by oral gavage. Each testing group contained three to five mice in each of four experiments. Each tumor from each treatment group was measured on indicated days, and all tumor sizes were then normalized to their size at day 0 of drug treatment. All data from all four experiments was then combined for statistical analysis, to compare every mouse from each treatment group. The total mice for all experiments included vehicle control (n=13), low-dose T (n=12), MBZ=12), high-dose T (n=12), low-dose trametinib+MBZ (n=12), and high-dose trametinib+MBZ (n=15). The results were expressed as the mean (±SD) of tumor volume in each group. After five weeks, mice were euthanized; tumors extracts were derived for immunoblot analysis.

Dosing

Trametinib doses were calculated relative to doses prescribed for patients, based on weight and body surface area for mouse and human, using the surface area to weight ratios ($m^2/kg$) described for mouse (0.02 kg/0.0066 $m^2$=3.0) and human (60 kg/1.6 $m^2$=37). This yields a similar constant to that calculated by Mosteller for humans: BSA (m2)=[SQRT (H (cm)×W (kg)]*60. Mouse "low dose" trametinib (0.1 mg/kg), adjusting for surface area=3/37*(0.1 mg/kg)=0.008 mg/kg, is therefore equivalent to a human dose of 0.008 mg/kg*60 kg (average body mass globally)=0.48 mg/person/day. For high dose trametinib, this is equivalent to 14.4 mg/person/day. By comparison, the dose for patients is 2 mg PO qDay (by mouth, twice a day). For MBZ, a dose of 40 mg/kg, adjusted for surface area constants 3/37 (mouse/human), is equivalent to 3/37*(40 mg/kg)*60 kg/person=195 mg. By comparison, patient doses range from 100 mg one time (pinworms) to 200 mg/kg per day for 12 weeks (hyatid disease in children) including doses up to 6 g per day. In summary, trametinib doses/[mouse BSA] bracket those prescribed for patients (from ¼- to 7-fold), and MBZ doses provided herein are much lower than those that have been safely used in patients and similar to those used in other preclinical studies.

Immunoblot Analysis

SDS-PAGE and transfer of separated proteins to nitrocellulose membranes were performed according to standard procedures. Membranes were stained with Ponceau S (0.1%) to verify equal loading and transfer of proteins, and then incubated with antibodies specific for pERK1/2 T202/Y204, pMEK1/2 S217/221, pBAD S-112, total BAD, total ERK1/2, total MEK1/2, BCL2 (Santa Cruz Biotech), BCLXL (Santa Cruz Biotech (Santa Cruz, Calif.)), cleaved PARP (Cell Signaling (Danvers, Mass.)), or GAPDH (Abeam (Cambridge, UK); loading control). Immune complexes were detected by incubation with appropriate horseradish peroxidase-conjugated antibodies to mouse or rabbit IgG (1:3000) and enhanced chemiluminescence (Pierce, Rockford, Ill.).

Fluorometric Caspase-3 Activity

Cytosolic extracts, derived from pooled floating and attached cells, were subjected to fluorometric caspase-3 activity assays using fluorescent tetrapeptide substrate specific for caspases-3 (Ac-DEVD-aminomethylcoumarin (AMC, Enzo Life Sciences, Ann Arbor, Mich.) as previously described (Simbulan-Rosenthal et al. *J. Biol. Chem.* 277: 24709-16 (2002)). Free AMC, generated as a result of cleavage of the aspartate-AMC bond, was monitored over 30 min with a Wallac Victor$^3$ fluorometer (Perkin-Elmer, Waltham, Mass.) at excitation and emission wavelengths of 360 and 460 nm, respectively. The emission from each sample was plotted against time, and linear regression analysis of the initial velocity (slope) for each curve yielded the activity.

Reverse-Phase Protein Arrays

Cell lysates were analyzed by reverse-phase protein array (RPPA). Samples were diluted to 0.5 mg/mL and dilutions printed on slides in triplicate. Slides were immunostained with 137 different antibodies specific for total proteins, or phosphorylated or cleaved products. Analytes measured were chosen based on their "actionability" (e.g. were known drug targets for FDA-approved drugs, drugs in clinical trials, or targets of other commercially-available compounds), as well as for their known involvement in tumorigenesis and cancer biology and components in key signaling pathways that control cell growth, motility, inflammation, autophagy, survival, differentiation and apoptosis. All antibodies have been pre-validated for specificity by immunoblot analysis. Intensity values were normalized to that of total protein for each sample stained with Sypro Ruby (Invitrogen Carlsbad, Calif.)). Unsupervised cluster analysis http://www.hiv.1an1.ov/content/sequence/HEATMAP/heatmap.html was performed for all proteins in the RPPA using the standard bootstrap method.

Statistical Analysis

The results shown are based on a single experiment in triplicate, and repeated in three independent experiments with essentially the same results. Data from triplicates of treatment groups were compared using Student's t-test or 2-way ANOVA (multiple comparisons) for significance, and p values of <0.05 were considered statistically significant. For tumor sizes, the rate-based. TIC (tumor/control) test of significance was used as described, using the author's template. The results are representative of 3 independent experiments with reproducible results. For determining synergism, the combination index ($\tau$) was calculated from single dose-response curves and combination experiments as $\tau=xA/XA+xB/XB$, in which, for a given cytotoxic effect, xA and xB are the concentrations of drugs A and B in the combination, and XA and XB are the concentrations of drugs A and B that achieve the same cytotoxic effect when given alone. A $\tau$ value of 1 indicates additivity, $\tau$ less than 1 indicates synergy, and $\tau$ greater than 1 indicates antagonism.

Results

Figure 1B:
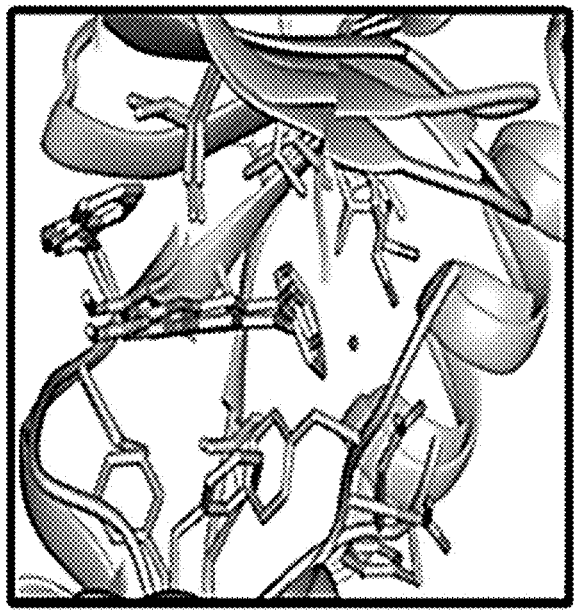
FIG. 1B shows a structure overlay of BRAFWT and BRAFV600E with MBZ.

In Silica Repurposing Technology and In Vitro Kinase Assays Show that MBZ Inhibits Mutant and Wild-Type BRAF Efforts to develop drugs targeting mutant BRAF led to FDA approval of vemurafenib in 2011 and dabrafenib in 2013. While these drugs either used alone or particularly when used in combination with MEK inhibitors such as trametinib or cobimetinib have been extremely successful at shrinking tumors, delaying disease progression and prolonging survival, resistance to them commonly develops at a median of 7-12 months, typically through the selection of variants exhibiting mutations in other kinase pathway members, most notably NRAS. The refined TMFS method provided herein, identified MBZ as a hit with a mode of inhibition that binds both wild type and V600E mutant BRAT (FIG. 1A, 1B). In addition, other MAPK pathway proteins including CRAF and MEK were identified. In-vitro assays confirmed that BRAF and MEK were inhibited by MBZ in the nM range (FIG. 1C), with MBZ inhibiting both BRAFV600E and BRAFWT with a $K_d$ of 210 and 230 nM, respectively, in agreement with previous results with a kinase screen of MBZ, chosen for its ability to inhibit colon cancer growth.

Both sorafenib, a pan-kinase inhibitor that interacts with BRAF, and RAF265, a RAF/VEGFR dual kinase inhibitor, bind to the DFG-out (indicating the positions of the three key amino acids aspartate, phenylalanine, and glycine) inactive conformation of BRAFWT and BRAFV600E at the ATP binding site. In contrast, vemurafenib and dabrafenib bind to the DFG-in active conformation of the ATP binding site. These active conformation inhibitors are highly BRAF-selective compared to other kinases. Structure-based modeling shows that MBZ binds both inactive and active conformations of BRAF (FIG. 1A, 1B). The BRAF structural model revealed that MBZ occupies the ATP-binding site and stabilizes both the active DFG-in and inactive DFG-out conformations. MBZ is surrounded by residues I463, V471, A481, K483, L505, L514, I527, T529, W531, C532, D594, and F595, and its binding is driven by hydrophobic and hydrogen bond interactions at the ATP site. An amide proton at the 2-position and a nitrogen atom at the N–1 position of the methyl N-(1H-benzimidazol-2-yl)carbamate moiety of MBZ form a significant hydrogen bond interaction with the backbone C=O and —NH of C532 in the kinase hinge regions of both the DFG-in and the DFG-out forms of BRAFWT and BRAFV600E. The methyl group connected to amide moiety of methyl N-(1H-benzimidazol-2-yl)carbamate forms a hydrophobic interaction with the indole ring of W531, and is suitably placed, whereas larger hydrophobic replacements would create steric hindrance due to space constraints in the binding site between the indole side chain of W531 and G534. Two interactions between MBZ and BRAFV600E, but not BRAFWT include: 1) an additional hydrophobic interaction between F593 and the benzimidazole moiety, and 2) a water-mediated hydrogen bond interaction between D594 and a keto group of the methyl N-(1H-benzimidazol-2-yl)carbamate moiety. These differences explain the slightly higher $K_d$ value observed for BRAFWT. MBZ does not interact with the BRAF lipophilic back pocket, unlike other BRAF inhibitors, lowering its affinity for BRAF and C-RAF.

Figures 1D, 1E:
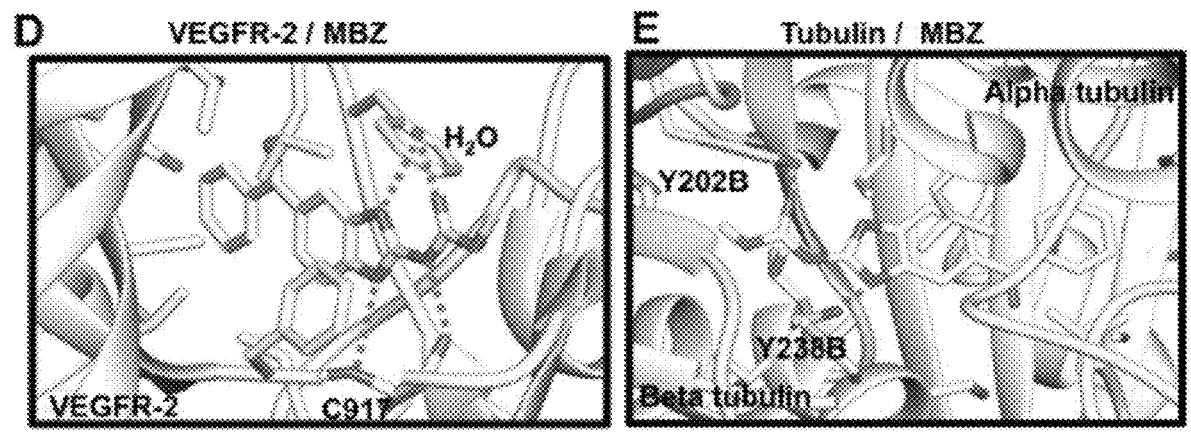
FIG. 1D shows a structural model of VEGFR-2 (PDB: 2OH4).
FIG. 1E shows a structural model of tubulin (PDB:3N2G; E) with MBZ. Critical binding site residues are displayed; hydrogen bonds shown as dotted lines and a water molecule shown as ball model.

TMFS analysis also reveals that MBZ interacts with VEGFR2 (FIG. 1D), consistent with its structural similarity to the benzimidazole-urea VEGFR2 inhibitor (PDB:2OH). However, MBZ showed more potency towards BRAF (FIG. 1C) than to VEGFR2, probably due to the absence of its interaction with residues lining the ATP site back pocket, which is more important for VEGFR2 than for BRAFV600E. In addition, the F918 phenyl ring of VEGFR2 restricts the diversified and non-planar conformation of MBZ, compared to the W531 indole ring of BRAF. Consistent with previous studies, MBZ also interacts with tubulin (FIG. 1E).

Figure 2A:
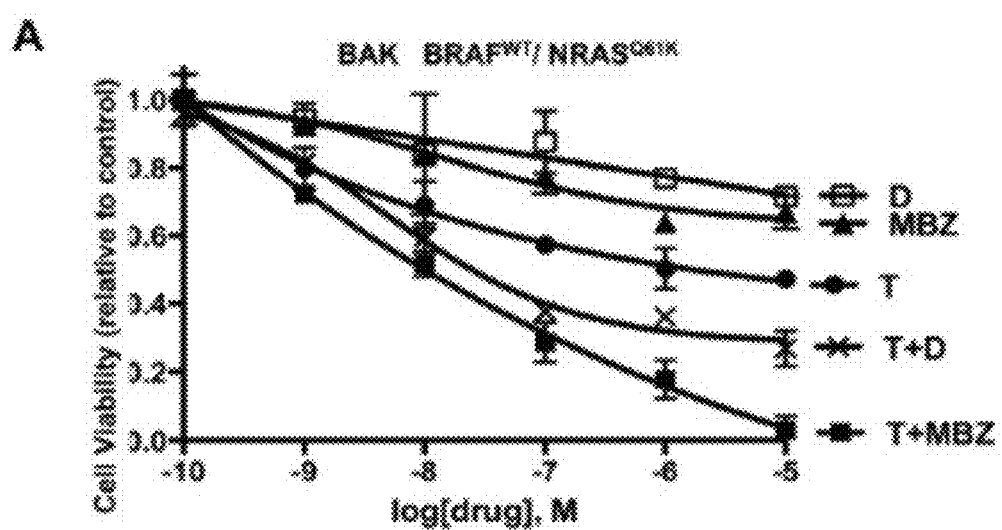
FIGS. 2A-2C show decreased viability of melanoma cells exposed to MBZ, dabrafenib (D), trametinib (T), or combinations of T+D or MBZ+trametinib. A) BAK (BRAFWT/NRASQ61K); B) BUL (BRAFWT/NRASQ61K); and C.) STU (BRAFV600K/NRASWT) melanoma cells were exposed to the indicated concentrations of MBZ, D, T, T+D or MBZ+trametinib (T+MBZ) for 72 h, and subjected to XTT cell viability assays, as described in the Examples. Error bars represent mean±SD for triplicates. Significant growth inhibition was observed at ≥1 nM for T or T+MBZ, ≥10 nM for MBZ alone, and ≥1 µM for D (2-way ANOVA). The results shown are based on a single experiment in triplicate; and repeated in three independent experiments with essentially the same results.
Figure 2B:
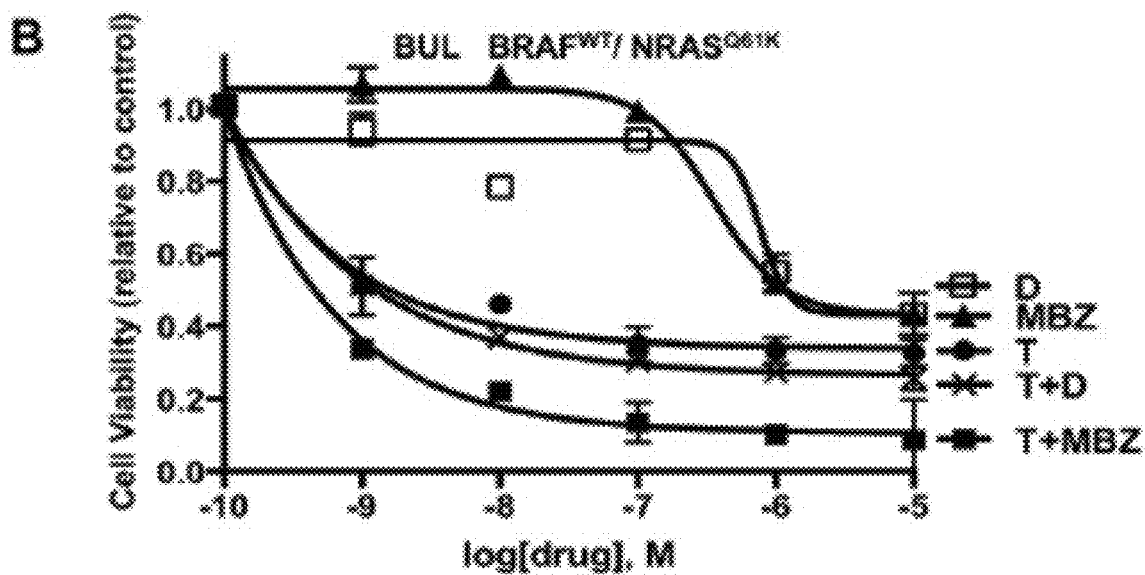
Figure 2C:
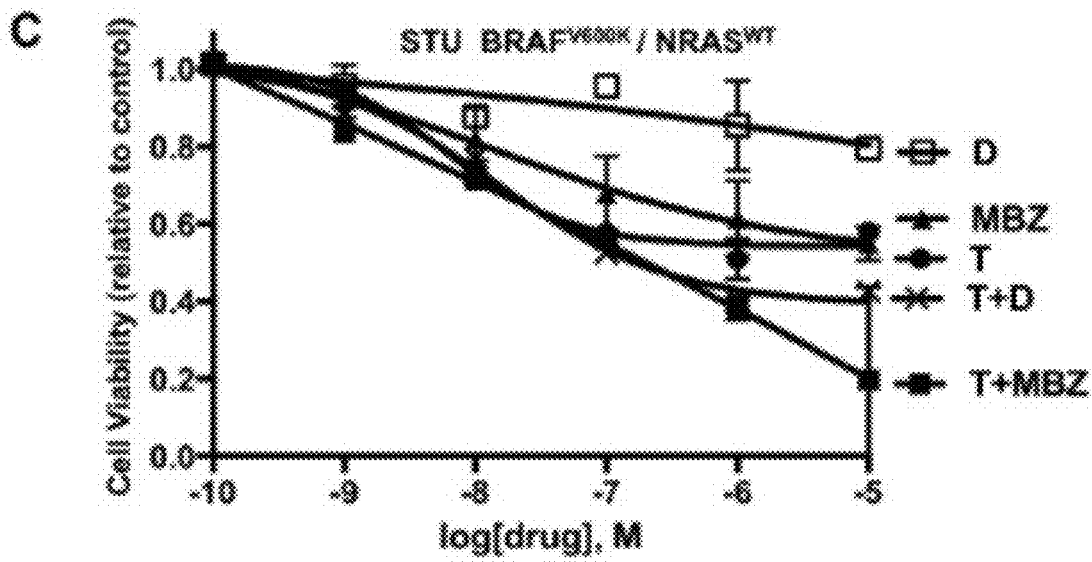

The Combination of MBZ and Trametinib is Cytotoxic to NRAS- and BRAF-Mutant Melanoma Cells Based on the ability of MBZ to target both mutant and wild-type BRAF, two patient-derived melanoma cell lines (BAK and BUL) harboring the same BRAFWT/NRASQ61K mutation profile and another melanoma cell line (STU) with a BRAFV600K/NRASWT mutation signature were exposed for 72 h to increasing concentrations of dabrafenib (D), trametinib (T), MBZ, or combinations of T+D or T+MBZ. XTT cell viability assays revealed that, while all three cell lines exhibited resistance to dabrafenib except at the highest doses tested, MBZ showed weak cytotoxic activity as a single agent, but synergized strongly with trametinib in both BAK and BUL cells, but was either antagonistic (at low concentrations) or additive (at high concentrations) in STU cells. T and D were also synergistic in BAK and BUL, but not STU, although maximum inhibition was greater in T+MBZ-treated cells (FIG. 2). Consequently, the MBZ+trametinib combination may represent a potential therapy in NRAS mutant melanoma cells.

Figures 3A, 3B:
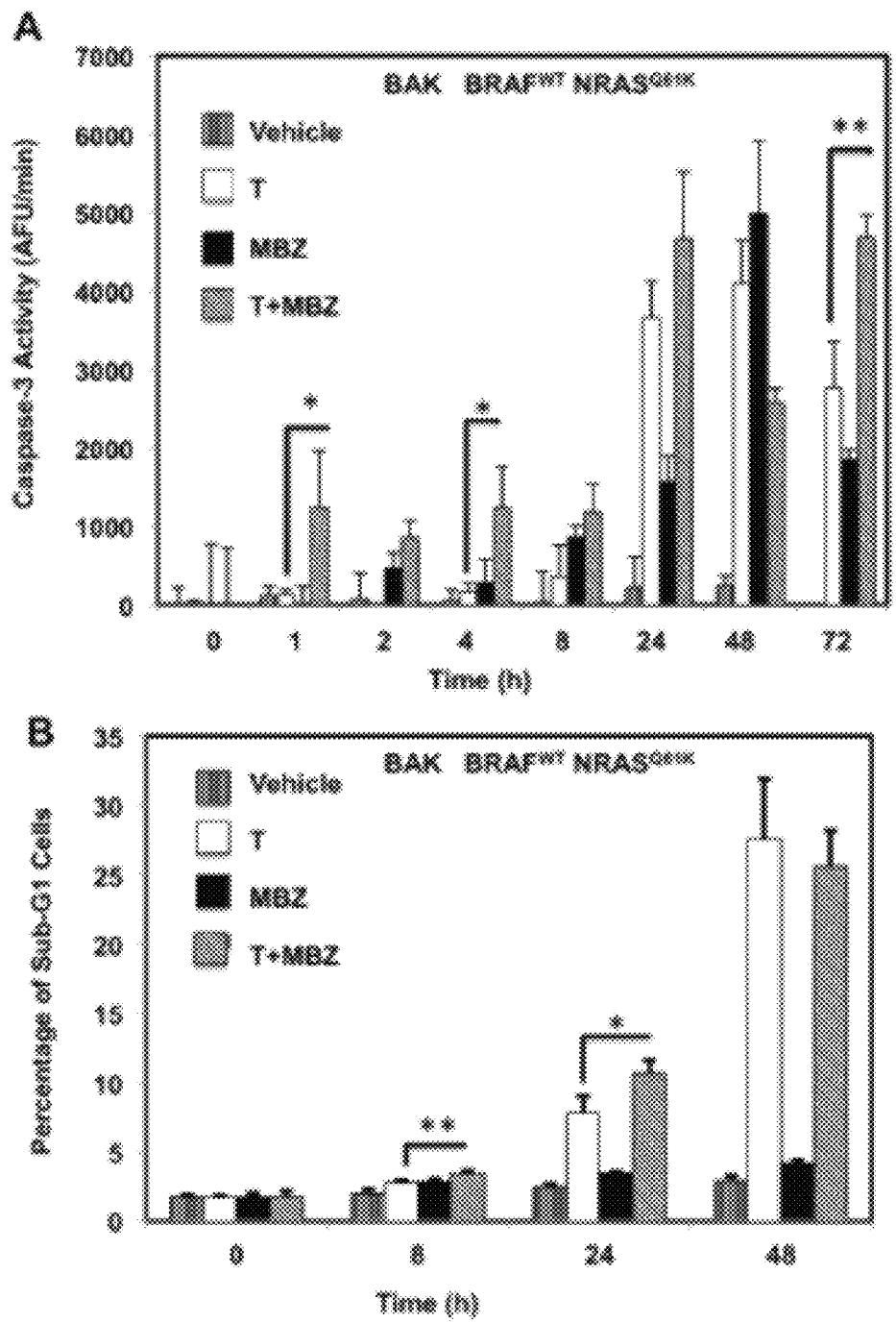
FIGS. 3A-J show that MBZ+trametinib induces apoptosis and decreases the percentage of melanoma cells in S phase of the cell cycle. BAK (A-E) or BUL (F-J) melanoma cells were exposed to 100 nM of MBZ, trametinib, or a combination of the two (T+MBZ); cytosolic extracts were derived at indicated times and subjected to fluorometric analysis using DEVD-AMC as a substrate (A, F). Other cells were fixed in EtOH, stained with PI, and subjected to FACS analysis to determine the number of cells in sub-G1 (B, G), S phase (C, H), G1 phase (D, I), or G2 phase of the cell cycle (E, J). Results are the mean±S.D. of three replicates of a representative experiment. Statistical analysis of T versus T+MBZ groups (A, B) and between vehicle and treatment groups (C-J); 1, 2, or 3 asterisks (*) represent p<0.05, p<0.001, and p<0.0001, respectively.

To determine whether the reduced cell numbers were due to inhibition of proliferation or increased cell death, apoptosis and cell cycle assays were performed in BAK and BIM melanoma cells. Caspase-3 activity (FIG. 3A, 3F), as well as a sub-G1 population (FIG. 3B, 3G) was induced earlier, and to a greater extent in cells exposed to T+MBZ than to either drug alone, indicating that this combination rapidly and robustly induces apoptosis. In both BAK and BUL cells, trametinib and/or the combination of T+MBZ also decreased the percentage of cells in S phase of the cell cycle at all time points, with concomitant increases in G2 and G1 phases of the cell cycle by 8 h or 24 h, respectively (FIG. 3C-3E, 3H-3J).

Figure 7:
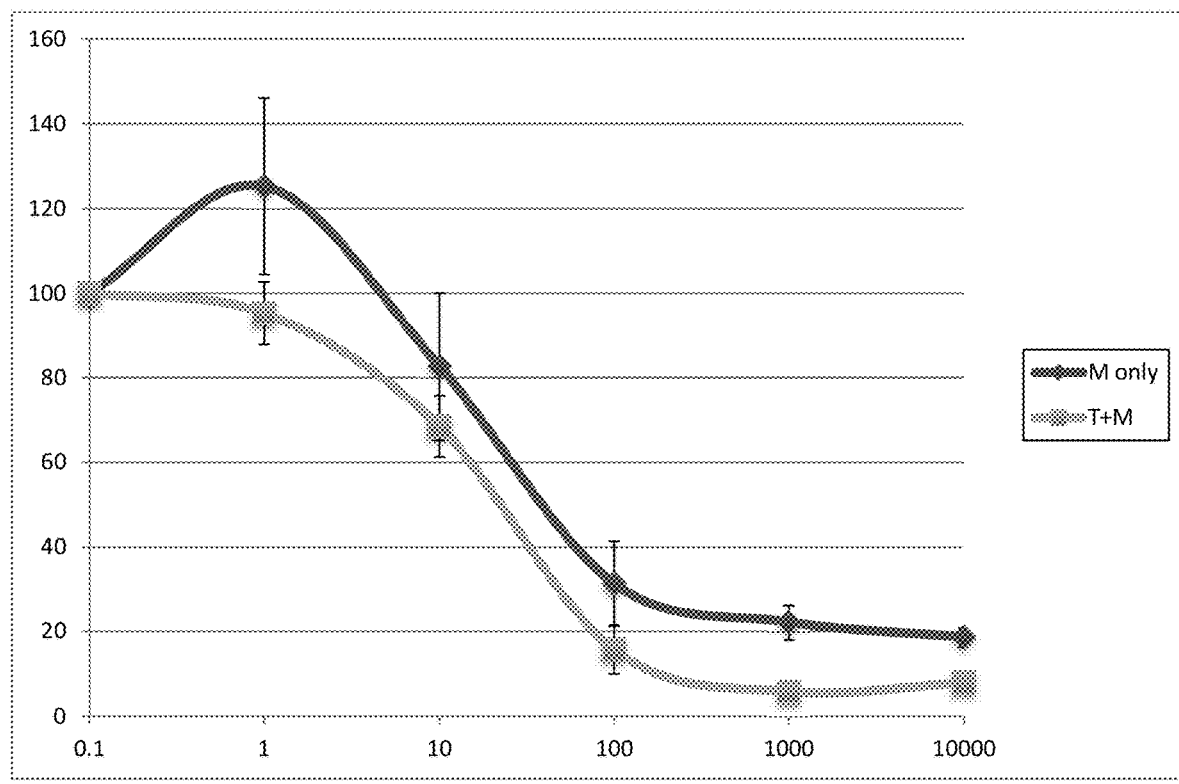
FIG. 7 shows that treatment of patient-derived cells harboring a BRAFWT/NRAS Q61K mutation profile with the indicated concentrations of mebendazole (shown in nM; diamonds) alone revealed sensitivity, which was further increased by adding the indicated concentrations of trametinib (squares; nM).

In studies with patient-derived metastatic melanoma cells harboring a BRAFWT/NRASQ61K mutation profile, treatment with mebendazole alone (diamonds), at the concentrations (nM) shown in FIG. 7, revealed sensitivity to treatment, which was further increased by adding the indicated concentrations of trametinib (nM) (squares). In additional studies, patient-derived cells harboring a BRAFWT/NRASQ61K mutation profile were separated into CD133+ populations and CD133− populations. CD133− cells were more sensitive to treatment with both mebendazole and the combination of mebendazole and trametinib.

PK Profile of Formulations

Figure 8:
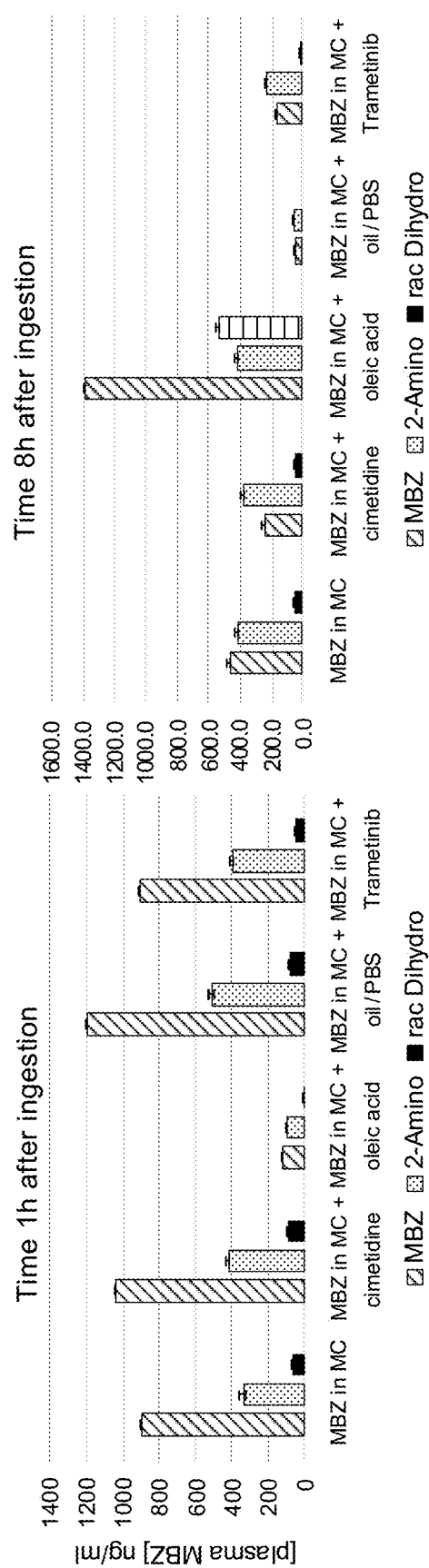
FIG. 8 shows the results of pharmacokinetic studies of mebendazole administered to athymic mice. Plasma mebendazole (left column) concentration and the concentrations of its two metabolites, 2ABB (center column) and RDM (right column), 1 hour and 8 hours after administration, using different formulations, are shown.

At one hour, there was no difference in exposure to MBZ or metabolites whether administered as different formulations or in combination with cimetidine or trametinib (P>0.05 by Kruskal-Wallis analysis of variance by ranks). At 8 hours, there was a significant difference in exposure to MBZ (P=0.009) or metabolites (P=0.012 for 2ABB; P=0.011 for RDM). Post-hoc analysis using an all Pairs Tukey-Kramer test revealed that: 1) oleic acid results in a higher MBZ (mean=1387 vs. 473 ng/mL) and RDM (mean=543 vs. 57 ng/mL) exposure and was comparable to methylcellulose exposure for 2ABB (mean=427 vs. 425 ng/mL); and 2) Trametinib co-administration resulted in a ~45% lower 2ABB metabolite exposure (mean=242 vs. 425 ng/mL) but did not alter MBZ nor RDM concentrations. Taken together, oleic acid is a lead formulation in terms of increased exposure to MBZ and metabolites at 8 hours (FIG. 8)

The Combination of MBZ and Trametinib Reduces Tumor Growth in Xenografts

To determine if MBZ and trametinib are effective against BRAFWT/NRASQ61K melanoma in vivo, BAK cells were xenografted into nude mice, and treated with MBZ, trametinib, or their combination. Two different doses of trametinib were administered to different groups of mice daily by gavage (0.1 mg/kg LDT, or 3 mg/kg HDT). A third group of mice was treated with a dose of MBZ similar to that used for helminthic infections (40 mg/kg on alternate days), while a fourth and fifth group of mice received a combination of MBZ and either LDT or HDT. These trametinib doses bracket those prescribed for patients (from ¼- to 7-fold), and our MBZ doses are much less than those safely used in patients based on dose per body surface area (BSA), and are similar to those in previous preclinical studies. The vehicle served as a control for the sixth group of mice.

Figures 4A, 4B:
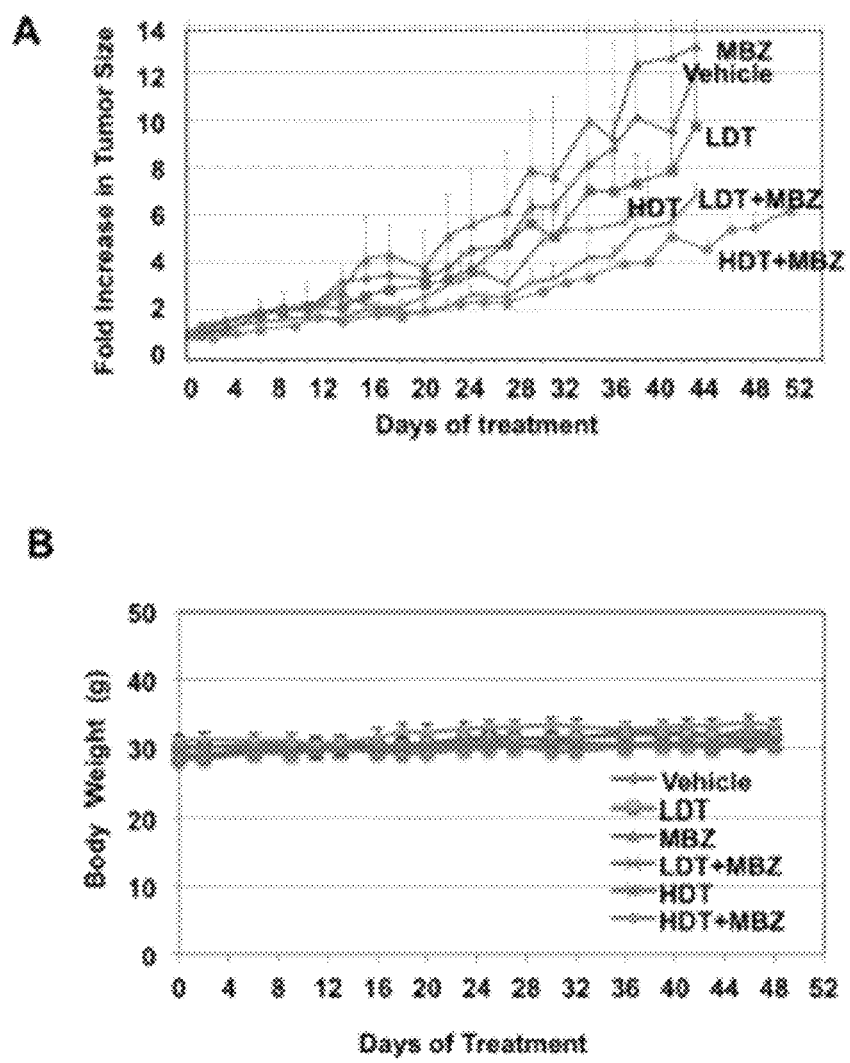
FIGS. 4A-4D show that MBZ+trametinib significantly inhibits tumor growth and phosphorylation of MEK and ERK in vivo. Athymic mice were injected with $3 \times 10^6$ BAK melanoma cells, and tumors were allowed to grow to a volume of 100 $mm^3$. Animals were then gavaged with vehicle emulsion control, 40 mg/kg/qad (every other day) MBZ, low dose trametinib (LDT; 0.1 mg/kg/qd (once a day)), high dose trametinib (HDT; 3 mg/kg/qd) or a combination of MBZ and LDT or HDT, A) Tumor widths and lengths were measured and volumes calculated as w2×l/2, where width is defined as the smaller of the tumor dimensions. Time 0 is the tumor volume on the first day of treatment; tumor sizes were normalized to their size at time 0 of drug treatment. B) Mice were weighed every other day and body weights (g) plotted over time. Data from four experiments were combined for statistical analysis, to compare every mouse from each treatment group. The total mice for all experiments included vehicle control (n=13), LDT (n=12), MBZ (n=12), HDT (n=12), LDT+MBZ (n=12), and HDT+MBZ (n=15). The results are shown as the mean (+SD) of tumor volume in each group. C) and D) ERK and MEK phosphorylation was suppressed in large (C) or small (D) tumor xenografts from mice treated with T+MBZ. Tumor extracts were derived from xenografts, then subjected to immunoblot analysis using antibodies specific for total BRAT, phospho-BRAF, ERK1/2, phospho-ERK1/2, total MEK1/2, phospho-MEK1/2, or GAPDH as a loading control.
Figures 4C, 4D:
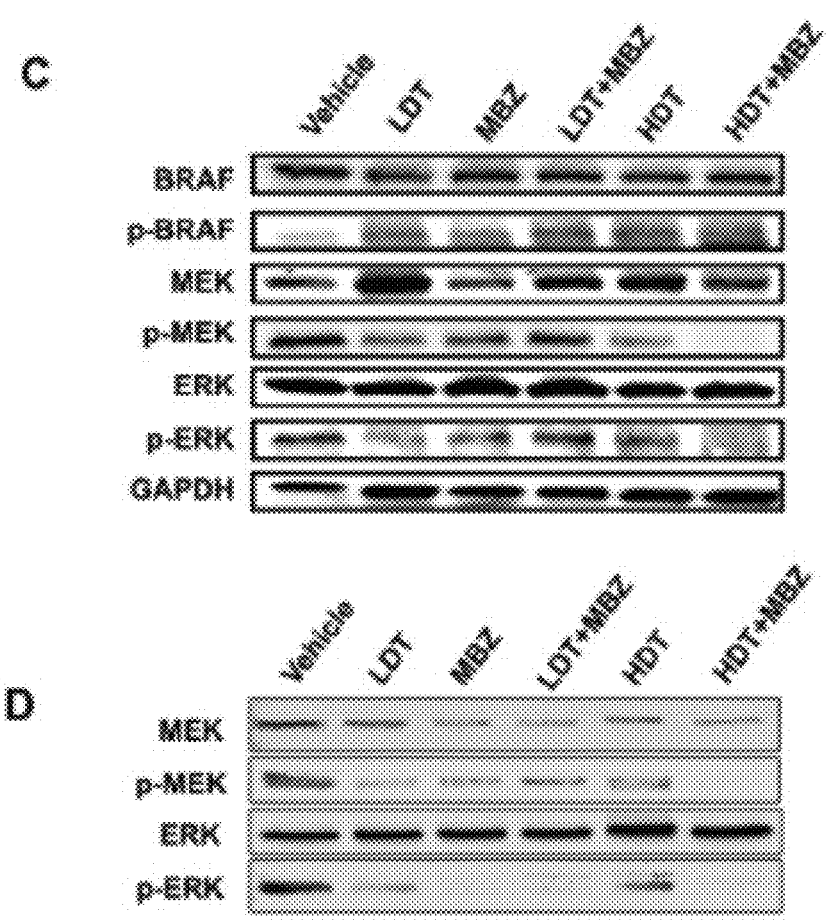

While trametinib as a single agent did not show any significant tumor-suppressive effects (HDT vs. control p=0.26; LDT vs. control p=0.65), tumor growth was significantly inhibited in mice treated with MBZ in combination with either high (HDT+MBZ vs. vehicle p=0.038) or low (LDT+MBZ vs. vehicle p=0.066) trametinib doses, although not quite to a significant level in the latter case, without loss in weight or any other obvious adverse effects (FIG. 4A, 4B). Remarkably, the HDT+MBZ combination group remained alive long after the other arms had been euthanized due to the size of the NRASQ61K melanoma xenografts at 42 days. Tumors from xenografts collected at the termination of the experiment were then subjected to immunoblot analysis to determine the protein levels and phosphorylation status of components of the MAPK pathway in vivo. Whereas MBZ and trametinib alone each demonstrate the ability to suppress MEK and ERK phosphorylation, only the combination of HDT+MBZ completely abrogated both MEK1/2 and ERK1/2 phosphorylation (FIG. 4C, 4D).

MBZ and Trametinib Target the MEK/ERK Pathway

Figure 5A:
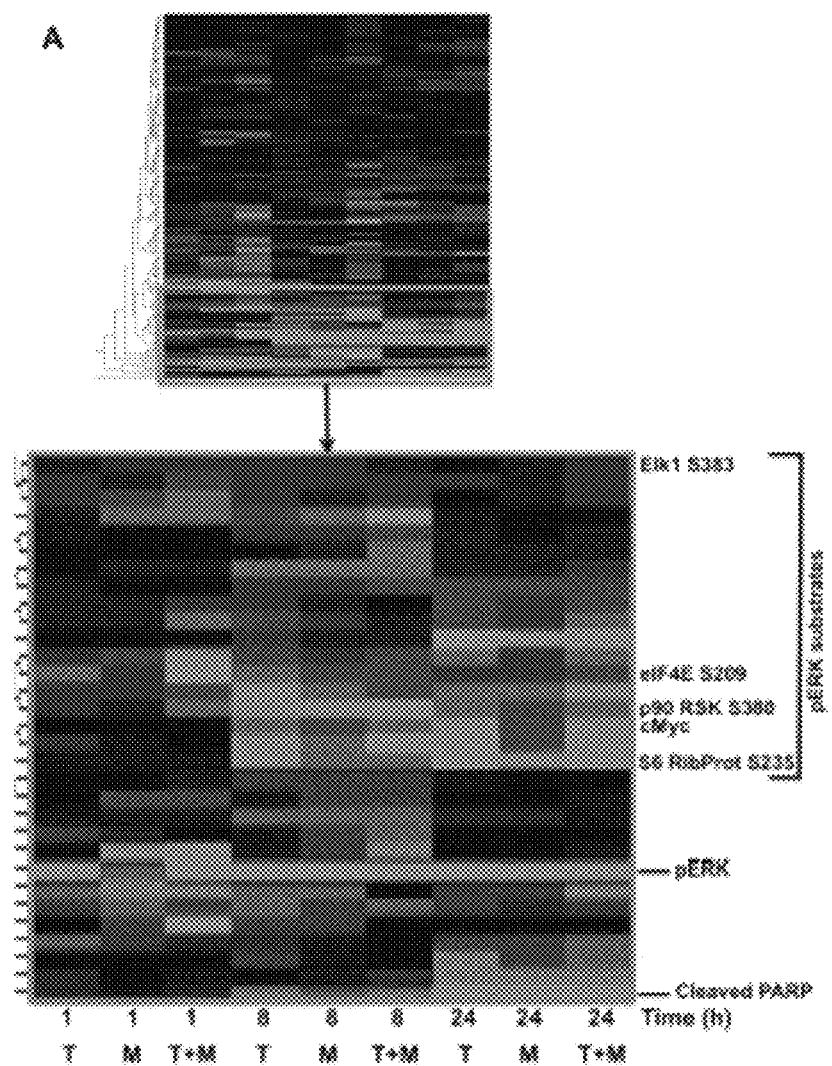
FIGS. 5A-H are RPPA (A) and immunoblot (B-E) analyses that reveal suppression of the MAPK pathway, including ERK and its downstream substrates in melanoma cells exposed to MBZ+trametinib. A. BAK cells were exposed to 100 nM of MBZ, trametinib, or a combination of the two. Cell extracts derived at indicated times were subjected to RPPA analysis, and unsupervised hierarchal clustering was used to generate a heat map as described in Materials and Methods. B)-E) Immunoblot analyses show marked attenuation of pMEK, pERK, as well as pBAD, coincident with increased levels of cleaved PARP, in melanoma cells exposed to MBZ+trametinib. BAK cells were treated with 100 nM of MBZ, trametinib, or a combination of the two for the indicated times; cell extracts derived and subjected to immunoblot analysis with antibodies specific for total MEK1/2, phospho MEK 1/2 (B), total ERK1/2, phospho-ERK1/2 (C), BCL2, BCLXL (D), phospho-BAD and cleaved PARP (E). F)-H) Immunoblot experiments were repeated with an additional melanoma cell line BUL, which harbors the same NRASQ61K mutation. Similar to BAK, BUL cells also exhibit a marked attenuation of ERK and MEK phosphorylation within 30 min of T+MBZ exposure, coincident with a loss of BAD phosphorylation and increased cleavage of PARP. All immunoblots were then reprobed with GAPDH as loading control.

Given the potential changes in tumor cell signaling and survival over the long time course of the xenografts, potential mechanisms by which MBZ+trametinib exerts its cytotoxic effects were examined using cultured BAK NRASQ61K melanoma cells. Cells were exposed to MBZ (10 nM or 100 nM), trametinib (10 nM or 100 nM), or a combination of the two for 1, 8, or 24 h, after which cell extracts were subjected to reverse-phase protein array (RPPA) analysis. Unsupervised hierarchal clustering of rows revealed that the phosphorylation of a number of proteins associated with the MEK/ERK pathway was down-regulated by MBZ, trametinib, or their combination, although the response to MBZ+trametinib (T±M) was more rapid and robust (FIG. 5A). Thus, phosphorylation of ERK and its downstream targets involved in translation, including p90RSK, ribosomal protein S6, and eIF4E were all concomitantly inhibited within 1 h of drug exposure, and remained hypophosphorylated for 24 h in the T+M groups; hypophosphorylated ELK1 S383 (a known ERK kinase substrate) was also associated with this cluster (FIG. 5A). Levels of LC3B and Beclin-1, key regulatory proteins that control autophagy, and known ERK pathway substrates, were also reduced in this cluster. Proteins characteristic of apoptosis were elevated with time, including the proteolytically activated form of caspase-3 and cleaved PARP, while total levels of the cell cycle progression protein cMYC were reduced (FIG. 5A), consistent with the effects of MBZ and trametinib on these two processes (FIG. 3).

Figures 5B, 5C, 5D, 5E:
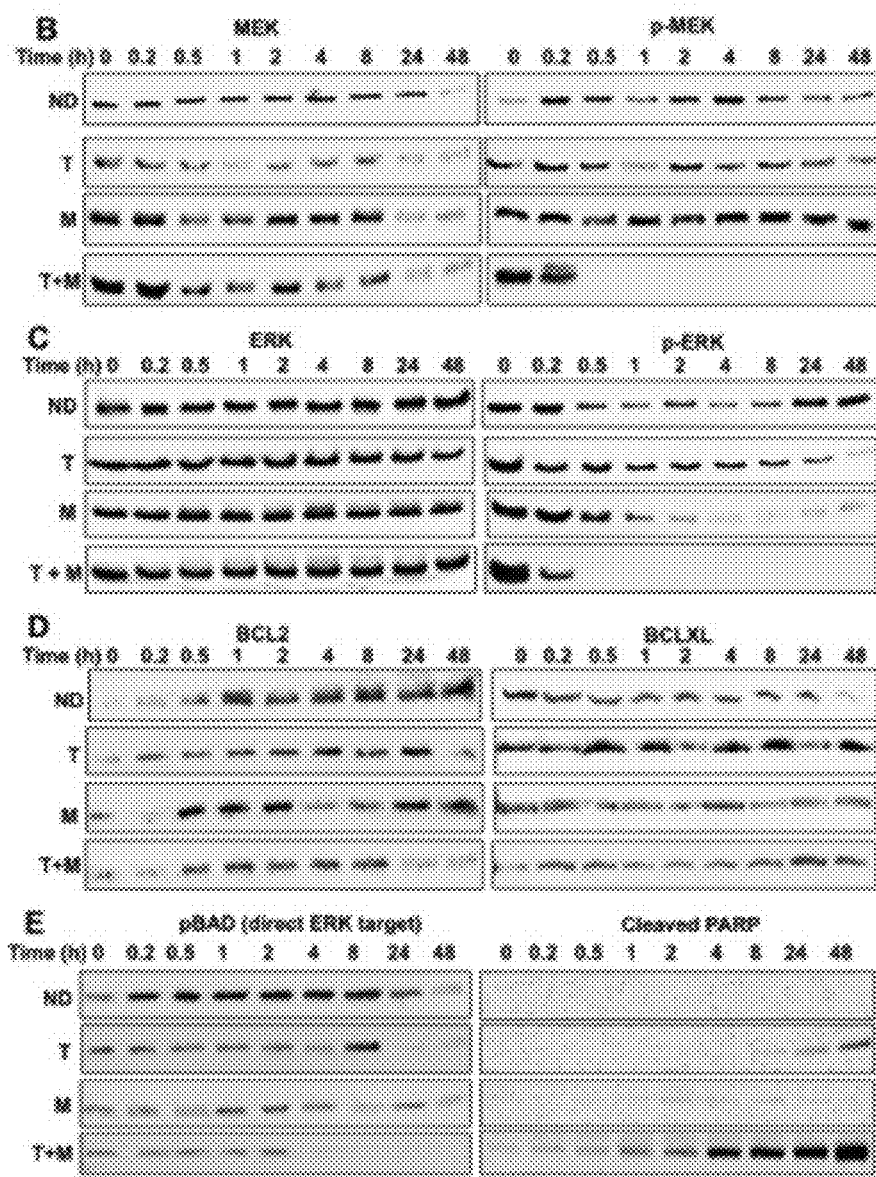

The potential pathway for early suppression of phospho-ERK and its targets, leading to apoptosis and cell cycle suppression was next examined by immunoblot analysis. Remarkably, whereas the pMEK1/2 S217/221 activating phosphorylation was not inhibited by trametinib or MBZ alone, their combination completely abolished detectable MEK phosphorylation within 30 min (FIG. 5B). While levels of total ERK1/2 remained constant throughout the time course for all treatment groups, the activating phosphorylation of ERK1/2 (T202/Y204) was diminished by MBZ or trametinib alone. However, the combination of MBZ+trametinib completely abrogated ERK phosphorylation, such that phospho-ERK was undetectable by 30 min of treatment (FIG. 5C). Consistent with the regulation of BCL2 levels by MEK/ERK, BCL2, but not BCLXL levels, were slightly reduced by MBZ+trametinib by 24 h (FIG. 5D). Further, cells treated with the MBZ+trametinib combination exhibited marked suppression of the inactivating phosphorylation of the pro-apoptotic ERK substrate BAD S11, coincident with a time-dependent increase in cleaved PARP (FIG. 5E), which is consistent with results observed by RPPA analysis (FIG. 5A).

Figures 5F, 5G, 5H:
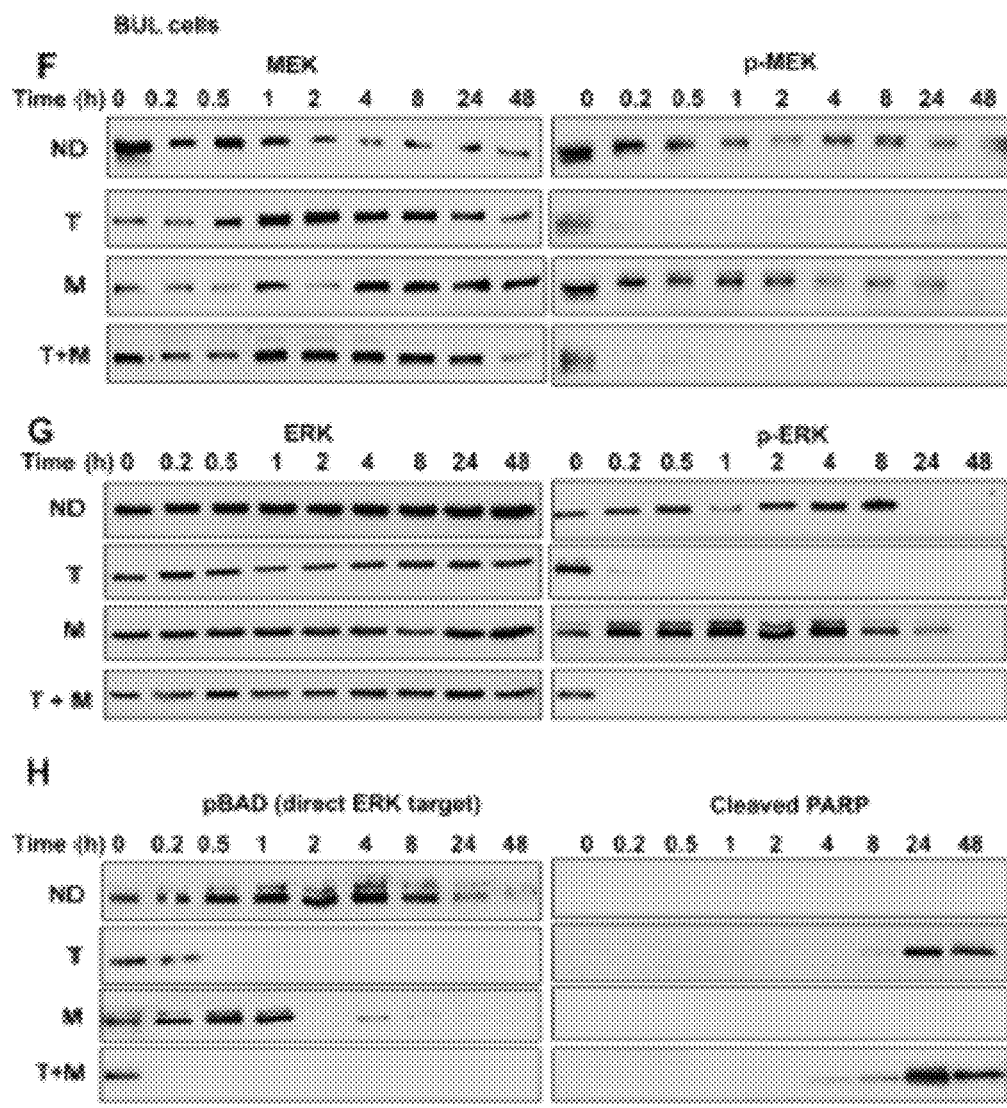
Figure 6:
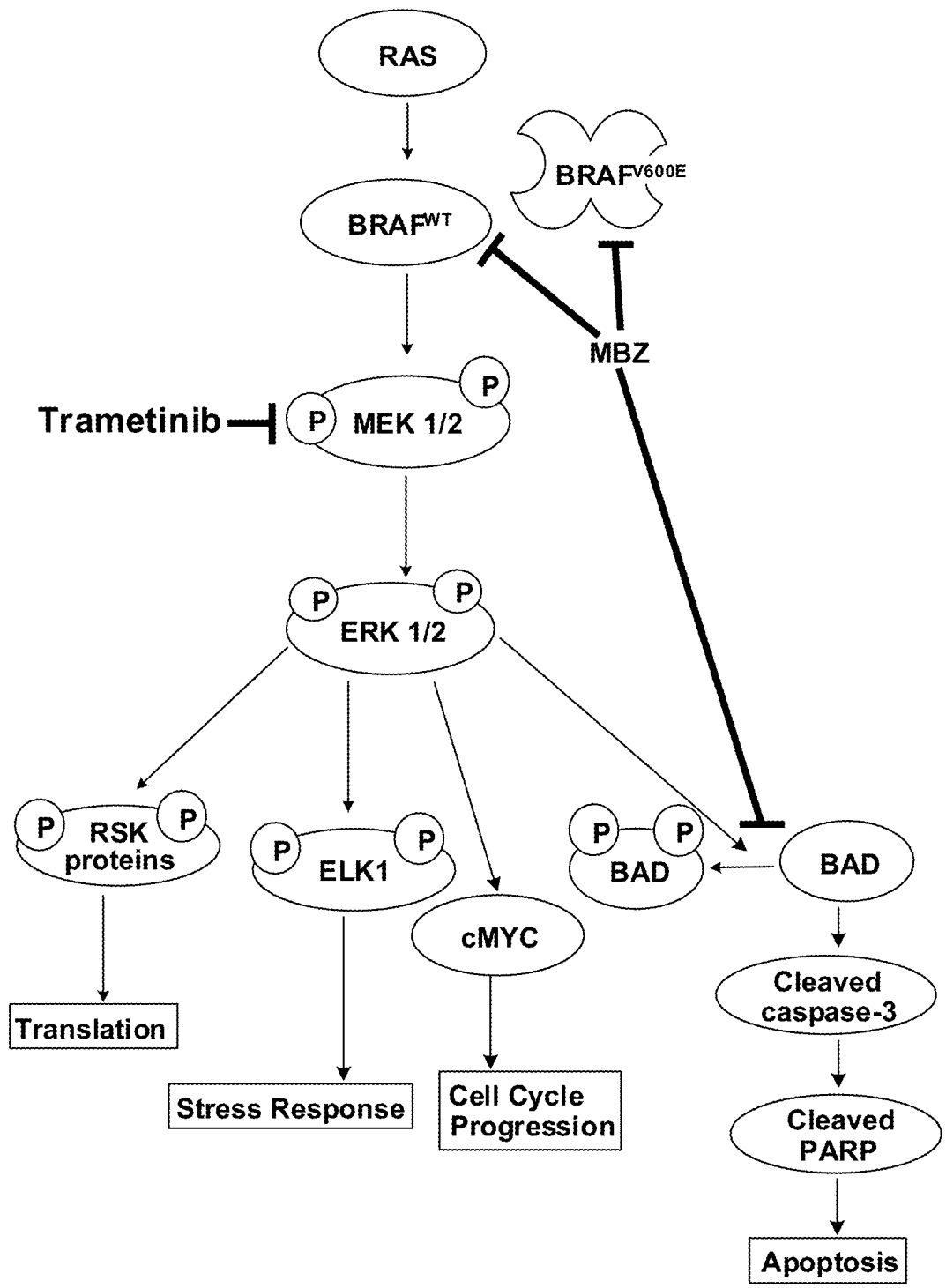
FIG. 6 is a schematic model of MBZ+trametinib mechanism of action in melanoma cells.

The immunoblot experiments were repeated with an additional melanoma cell line BUL, which harbors the same NRASQ61K mutation. Similar to BAK, BUL cells also exhibit a marked attenuation of ERK and MEK phosphorylation within 30 min of T+MBZ exposure, coincident with a loss of BAD phosphorylation and increased cleavage of PARP (FIG. 5F-5H), demonstrating that both mutant NRAS cells respond strongly to the combination of these two drugs. Taken together, a model for suppression of melanoma growth by MBZ+trametinib is shown in FIG. 6.

MBZ interacts with VEGFR in silico and MBZ interacts with additional kinases in vitro, including BCR-ABL and BRAF. TMFS was used to show the nature of the interactions between MBZ, and VEGFR, and with BRAFWT or BRAFV600E. These studies provided the novel finding that MBZ binds both the active and inactive forms of these BRAF proteins. NRASmut/BRAFWT melanoma cells, which account for about 21% of all melanoma cases have been particularly recalcitrant to treatment, with overall survival times that are shorter than those of patients with melanoma harboring BRAF mutations, and do not respond to BRAFV600 inhibitors such as vemurafinib and dabrafenib. In fact these inhibitors actually enhance growth of NRASmut/BRAFWT tumors by paradoxically further activating the MAPK pathway through induced conformational changes in wild type RAF isoforms, inducing dimerization, membrane localization, and activation by RAS. The advantages of MBZ are that 1) it interacts with both the active and inactive forms of BRAF, 2) it binds wild type or mutant BRAF with almost equal affinities, and 3) it has very low affinity for CRAF, and therefore would not be expected to stimulate tumor growth.

Consistent with the TMFS and kinase assays described herein, MBZ is toxic to patient-derived melanoma cells harboring either WT or mutant BRAF in the presence of trametinib. Further MBZ+trametinib strongly suppressed the growth of BRAFWT/NRASQ61K melanoma xenografts, and dramatically inhibited ERK1/2 phosphorylation within 10 min. This also blocked phosphorylation of its downstream targets resulting in suppression of proliferation, inhibition of autophagy, and induction of apoptosis; at least in part via suppression of ERK-mediated phosphorylation of BAD, ELK1, decreased expression of Beclin and LC3B, and decreased BCL2 levels. In light of the relative non-toxicity of MBZ, these studies show that the MBZ-trametinib combination is a compelling candidate as a therapeutic for patients with metastatic NRAS mutant melanoma.

Figures 3C, 3D, 3E:
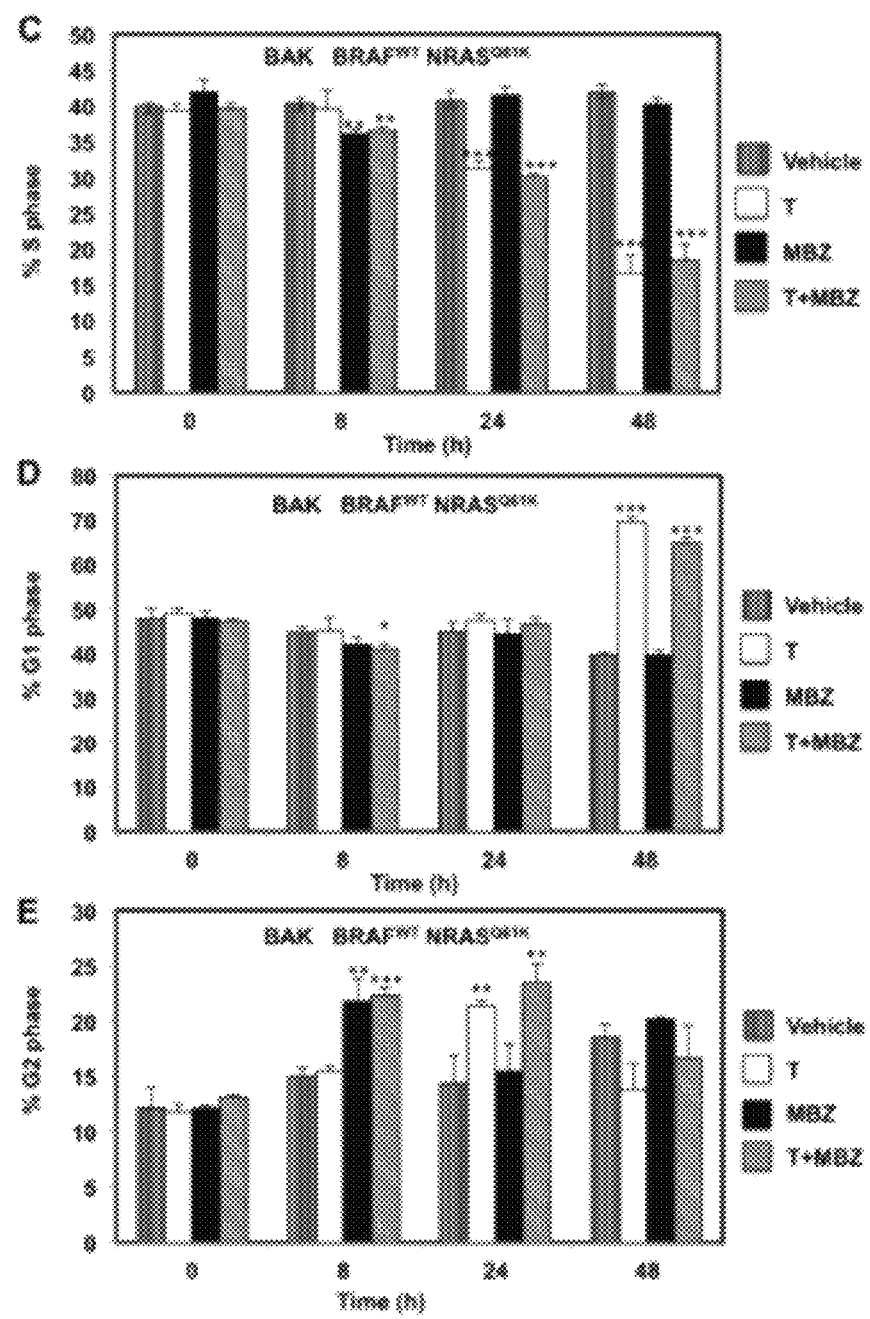
Figure 3F:
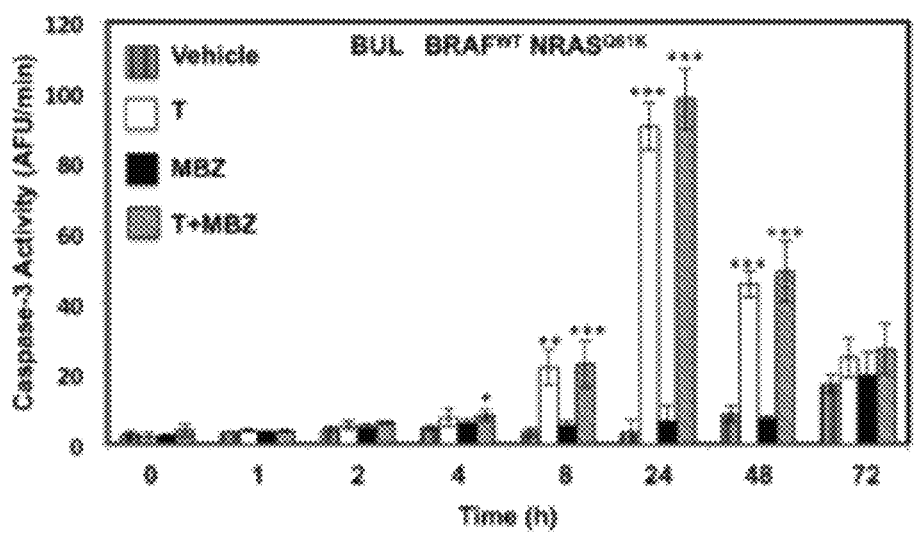
Figure 3G:
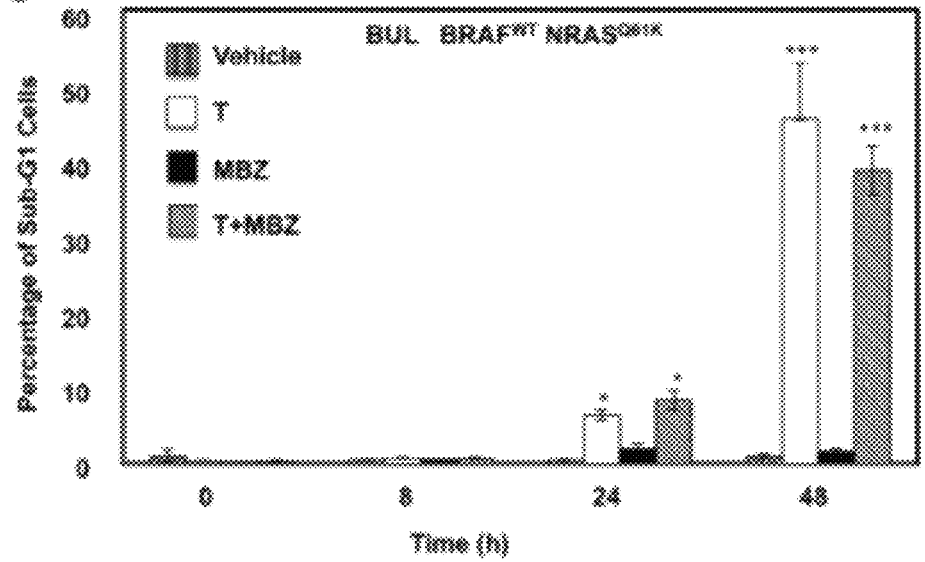
Figures 3H, 3I, 3J:
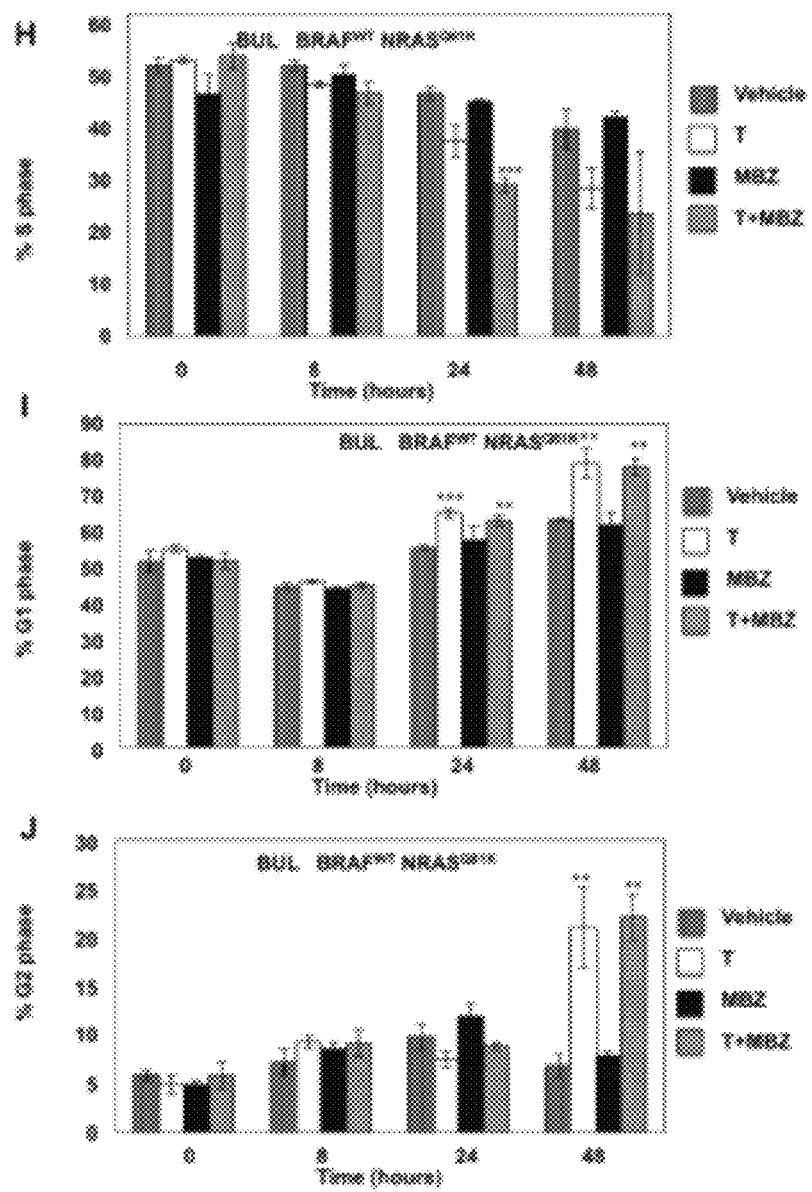

In the mouse xenograft model studies provided herein, MBZ did not work as a monotherapy, but did strongly enhance the effects of trametinib (FIG. 4). These results demonstrate that MBZ+trametinib reduces BCL2 levels, as well as BAD S112 phosphorylation, both of which can be explained by the inhibition of MEK/ERK by MBZ+trametinib, although some contribution by a lower affinity MBZ-tubulin interaction cannot be ruled out. Additionally, inhibition of phospho ELK1 S383 was observed at all time points and treatments, a mechanism previously shown to mediate sorafenib-induced endometrial carcinoma apoptosis by lowering MCL1 levels (FIG. 5A). An MBZ-induced increase in G2 levels was noted (FIG. 3E, 3J). It should be noted that the BAK cells used in the current study harbor a difficult to treat mutation profile.

The results provided herein suggest that BRAF is a major target for MBZ (FIG. 1C). Oral MBZ can reach peak serum concentrations similar to those used in these studies. For example, in patients treated with chronic MBZ for hydatid disease, a dose of 10 mg/kg/day resulted in a mean peak plasma level of 470 nM, with some variability between patients (0.34-1.69 µM), matching half the dose (or ½4th BSA-adjusted dose) administered to the mice in this study (40 mg/kg/qad; FIG. 4), and a plasma concentration equivalent to an $IC_{80}$ in cultured NRAS cells (FIG. 2A). MBZ significantly enhanced efficacy of trametinib at 0.1 mg/kg/day (LDT) or 3 mg/kg/day (HDT). These trametinib doses/[mouse BSA] bracket those prescribed for patients (from ¼- to 7-fold), are similar to those used in patients. Therefore, the trametinib dose-dependent reduction in growth of the MBZ-trametinib treatment groups is useful in treating NRAS tumors, and could work in concert with other drugs.

Example 2

Clinical Trial Plan Study Design

The following is an example of phase I trial evaluating the safety and tolerability of the combination of trametinib and MBZ in patients with metastatic melanoma harboring an NRAS Q61R/K mutation. Up to 3 doses are examined in the dose escalation portion of the phase I study to determine the maximum tolerated dose (MTD) of the combination of trametinib and MBZ. Once the MTD has been established, two expansion cohorts are accrued: (1) NRAS Q61R/K mutant metastatic melanoma, including patient at MTD in dose escalation phase, and (2) BRAFV600 mutant metastatic melanoma with phospho-ERK reactivation. These cohorts are studied to further assess the feasibility and safety of the combination and confirmation of the RP2D as well as preliminary evidence of antitumor activity.

The population in the phase I dose escalation study consists of patients at least 18 years of age with histologically confirmed diagnoses of metastatic melanoma harboring a NRAS Q61R or Q61K mutation, as determined by a FDA-approved test. Patients with measurable tumors as defined by Response Evaluation Criteria in Solid Tumors (RECIST), v1.1) and meeting study selection criteria detailed above are eligible for enrollment in this trial.

A standard 3+3 dose escalation design is used to determine the MTD and to define a preliminary toxicity profile for the combination of trametinib and MBZ, as described in this protocol. In addition, pharmacokinetics are collected when MBZ and trametinib are used in combination and to correlate with pharmacodynamics responses (clinical response, toxicity, and laboratory biomarkers). It is expected that 2 to 18 subjects will be required in a phase I dose escalation study to determine the MTD. Patients must begin therapy within 14 days of registration.

Figure 9:
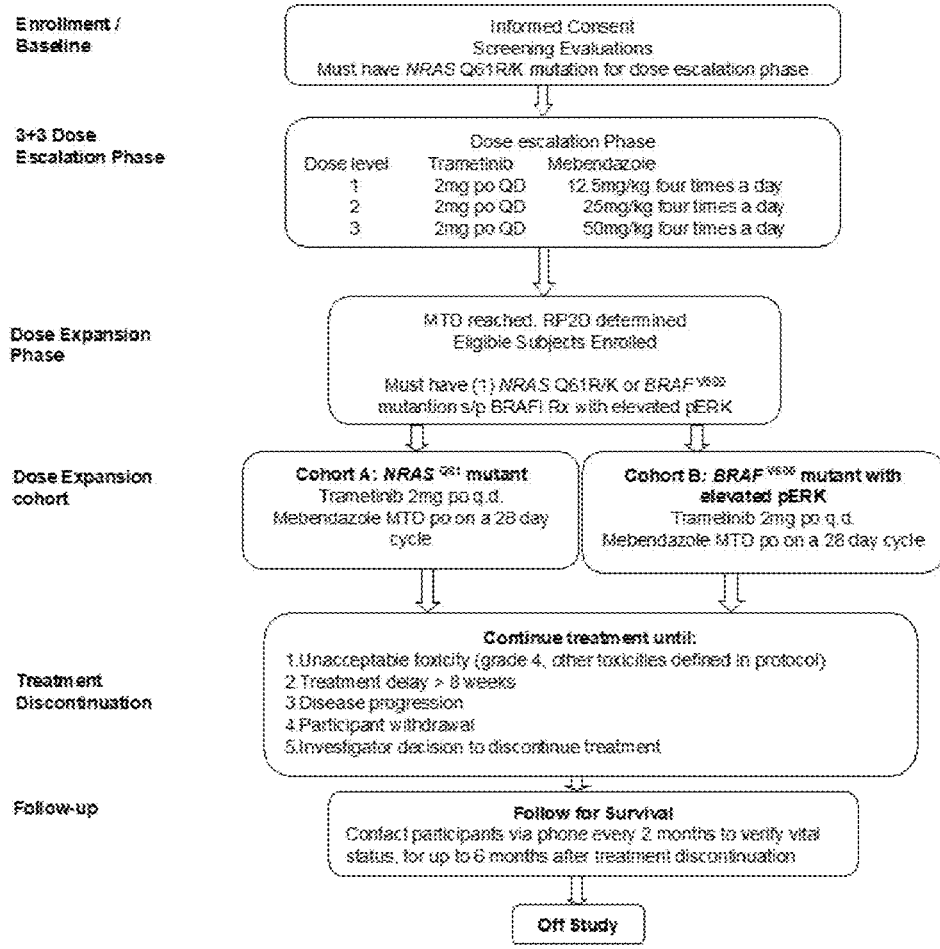
FIG. 9 is a schematic of a clinical trial for administration of mebendazole and trametinib. In this non-limiting example trametinib is administered orally (p.o.), once daily (QD), in combination with mebendazole, which is administered four times a day.

An expansion cohort is planned to enroll up to 15 additional patients from (1) NRAS Q61R/K mutant metastatic melanoma, and (2) BRAFV600 mutant metastatic melanoma with phospho-ERK reactivation. Prior to enrollment, each participant will have a tissue biopsy, or an archived tissue to confirm 1. NRAS Q61 mutation status (cohort A), or 2. A pERK reactivation by immunohistochemistry in patients with BRAFV600 mutation (cohort B). Safety and toxicity of the treatment combination will also be monitored with expected less than 33% dose limit toxicity (DLT). FIG. 9 is a schematic of an exemplary clinical trial. Integral biomarkers and correlates will also be assessed, as set forth below in Tables 1 and 2, respectively.

TABLE 1

| Integral Biomarker | Assay | Tissue/Body Fluid Tested and Timing of Assay |
|---|---|---|
| pERK activation (M) | Immunohistochemistry (IHC) | Tumor samples tested during eligibility evaluation for cohort B, and a post-treatment biopsy after cycle#1 (+/−4 days) in both cohort A and B |
| NRAS mutation analysis (M) BRAF | Sanger sequencing | Tumor samples will be tested during eligibility evaluation for cohort A prior to enrollment. |
| Pharmacokinetics | Drug concentrations for mebendazole and metabolites and trametinib will be assessed by LC/MS/MS. | A single dose PK will be obtained on the first dose in combination on Cycle 1, Day 1 (Phase 1) and trough samples at the time of other correlative studies (steady-state concentrations for expansion cohorts) |

TABLE 2

| Correlative Objective Name of Correlate | Assay | Tissue/Body Fluid Tested and Timing of Collection |
|---|---|---|
| Tissue Ki67 level | Immunohistochemistry (IHC) | A tumor sample is obtained at the end of cycle#1 treatment (+/−4 days) to assess proliferative index of the tumor after treatment |
| Tissue p27 level | Immunohistochemistry (IHC) | A tumor sample is obtainedat the end of cycle#1 treatment (+/−4 days) to assess proliferative index of the tumor after treatment |
| Tissue TUNEL assay | Terminal deoxynucleotidyl transferase + dUTP nick end labeling assay. | A tumor sample is obtained at the end of cycle#1 treatment (+/−4 days) to assess apoptotic index of the tumor after treatment |
| Tissue Bcl2 phosphorylation assay | Tissue bcl2 phosphorylation assay is performed by Western blot analysis | A tumor sample is obtained at the end of cycle#1 treatment (+/−4 days) to assess apoptotic index of the tumor after treatment |

Abbreviated Eligibility Criteria
1. Patients must have histological or cytological confirmed melanoma that is metastatic.
2. Patients must have melanoma that is documented to contain NRAS Q61 mutation by a CLIA-approved test.
3. Patients who are enrolled in a dose expansion cohort (cohort B) must have melanoma that is documented to contain a BRAF V600E mutation previously treated with BRAF inhibitor with documented activation of pERK by immunohistochemistry analysis at Georgetown-Lombardi Histopathology Shared Resource.
4. All females of childbearing potential must have a blood test or urine study within 24 hours prior to registration to rule out pregnancy. Patients must have measurable disease (cutaneous lesions measuring at least 1 cm will be considered measurable). Baseline CT or MRI scans of measurable disease sites must be performed within 4 weeks of study entry. This is only required in dose expansion cohorts.
5. Naïve untreated patients or patients who have received 3 or less prior treatments Note: prior adjuvant therapy [e.g. IFN, IL-2 therapy, any other immunotherapy], prior chemotherapy [e.g. dacarbazine, carboplatin, paclitaxel, or temozolomide], or prior immunotherapy [e.g. ipilimumab, IL-2 therapy, anti-PD1/PD-L1 therapy, any other immunotherapy] is permitted for patients with previously treated metastatic disease.
8. Patients must have an ECOG performance status of 0, 1, or 2.
9. Patients must have the following baseline laboratory values:
   a) White Blood Count $\geq 3,000/mm^3$
   b) Absolute Neutrophil Count $\geq 1,500/mm^3$
   c) Platelet Count $\geq 100,000/mm3$
   d) Serum creatinine $\leq 1.5 \times$ upper limit of normal (ULN) or serum creatinine clearance (CrCl)$\geq 40$ ml/min (CrCl=Wt (kg)$\times$(140-age)*/72$\times$Cr. level, *female$\times$ 0.85)
   e) Aspartate aminotransferase (AST)/alanine aminotransferase (ALT)$\leq 3 \times$ULN ($\leq 5 \times$ULN for patients with documented liver metastases)

f) Alkaline Phosphatase ≤2×ULN (≤5×ULN for patients with known liver involvement and ≤7×ULN for patients with known bone involvement)
g) International Normalized Ratio (INR)≤1.5 and aPTT within 1.1×ULN
h) Total Bilirubin ≤1.5×ULN
i) UPC ratio <1.0 at screening or 24 hours urine protein <1 gm (Appendix D)
10. QTc interval ≤480 ms Patients must have the ability to understand and the willingness to sign a written informed consent document.

Outcomes

Primary Endpoint

All patients who receive at least one dose of each medication will be reported for safety evaluation. Patients who received more ≥85% of the total 28 day cycle dose of both trametinib and MBZ (more than 23 days of treatment) will be included in the determination of the MTD (and subsequent RP2D).

Secondary Endpoints

The following outcomes will be followed as secondary endpoints:

Objective Response Rate (ORR) (partial response and complete response) by RECIST criteria in two distinct expansion cohorts of patients: stage IV NRAS mutant (cohort A); or $BRAF^{V600E}$ melanoma resistant to BRAF inhibitor treatment with evidence of pERK reactivation (cohort B) (n=15 evaluable patients in each cohort) while on the RP2D.

Disease Control Rate (DCR) (stable disease/partial response/complete response) for treated and evaluable patients (complete 2 cycles of therapy) while on a particular dose with this treatment regimen, as defined by RECIST criteria. Patient in dose escalation phase at RP2D will be included in this analysis.

Trametinib and mebendazole exposure will be assessed after a single dose during the Phase I dose escalation to assess whether adequate exposure is achieved. In addition, steady-state concentrations of both drugs will be assessed in the dose-expansion cohorts to correlate with outcomes (efficacy, safety, and laboratory biomarkers)

Total and phosphorylated ERK level in tumor biopsies prior to and subsequent to therapy with combination of trametinib and MBZ. This will be measured in dose-expansion cohorts only.

Changes in PD markers that reflect tumor proliferation, and apoptosis (Ki67, p27, Bcl2 staining, and TUNEL assay). These markers will be measured in dose-expansion cohorts only.

Descriptive statistical methods will be used to summarize the data from this study. Unless stated otherwise, the term descriptive statistics refers to number of subjects (n), mean, median, standard deviation (SD), minimum, and maximum for continuous data and frequencies and percentages for categorical data. For categorical endpoints, ORR and DCR rates will be described with the corresponding 95% exact confidence intervals. Plasma concentration and pharmacokinetic (PK) parameters of trametinib and MBZ and metabolites will be presented as descriptive statistics in tabular and graphic form. PK parameters (e.g., total and maximal exposure, half-life and apparent clearance) will be determined using non-compartmental methods. Appropriate nonparametric statistics will be utilized to correlate PK parameters with efficacy outcomes. All statistical analyses will be conducted with the JMP or SAS® (version 9.3 or higher) software packages.

Statistical Considerations

This is a Phase I study to determine the MTD and recommended Phase II dose for MBZ when administered with trametinib at 2 mg per daily, and to evaluate the preliminary antitumor efficacy of the studied drug. Since there are no anticipated additive toxicities and thus the expected DLT is less than 33%, the classic 3+3 design was chosen for dose escalation (in three dose levels) with an expansion cohort at the identified MTD. The sample size is variable. It is anticipated that 2-18 evaluable patients will be treated in the dose escalation phase. 15 patients will be enrolled in the dose expansion cohort. The expansion size of 15 is chosen as it gives reasonable statistical power for initial estimate and assessment of the association between the biomarkers (e.g, PD markers; and total and pERK levels) and patient response. For example, if 5 or 7 responses are observed in a cohort of 15 patients, we would have 77%-82% power to show a moderate difference of 1.6 standard deviations in a specific marker between the responders and non-responders at a significance level of 5%, and the lower limit of the one-sided 90% CI for the ORR is 17% and 28%, respectively.

What is claimed is:

1. A method for treating a melanoma comprising administering to a subject with a melanoma tumor
   a) mebendazole; and
   b) trametinib,
   wherein the melanoma tumor expresses wildtype BRAF, wherein mebendazole inhibits wildtype BRAF, and wherein mebendazole and the MEK inhibitor are administered in effective amounts for a synergistic effect.

2. The method of claim 1, further comprising screening for one or more predetermined mutations in the NRAS gene in the tumor in the subject.

3. The method of claim 1, further comprising screening for specific mutations that are indicative of resistance of one or more therapies for melanoma.

4. The method of claim 1, wherein the subject is resistant to treatment with an inhibitor of mutant BRAF monotherapy.

* * * * *